United States Patent
Molettiere et al.

(10) Patent No.: US 8,849,610 B2
(45) Date of Patent: Sep. 30, 2014

(54) TRACKING USER PHYSICAL ACTIVITY WITH MULTIPLE DEVICES

(71) Applicant: Fitbit, Inc., San Francisco, CA (US)

(72) Inventors: Peter Andrew Molettiere, San Francisco, CA (US); Shelten Gee Jao Yuen, Berkeley, CA (US); Jung Ook Hong, Emeryville, CA (US); Andrew Cole Axley, Oakland, CA (US); James Park, Berkeley, CA (US)

(73) Assignee: Fitbit, Inc., San Francisco, CA (US)

( * ) Notice: Subject to any disclaimer, the term of this patent is extended or adjusted under 35 U.S.C. 154(b) by 0 days.

(21) Appl. No.: 14/178,232

(22) Filed: Feb. 11, 2014

(65) Prior Publication Data

US 2014/0164611 A1 Jun. 12, 2014

Related U.S. Application Data

(60) Continuation-in-part of application No. 13/959,714, filed on Aug. 5, 2013, which is a continuation-in-part of application No. 13/693,334, filed on Dec. 4, 2012, now Pat. No. 8,548,770, which is a division of application No. 13/667,229, filed on Nov. 2, 2012, now Pat. No. 8,437,980, which is a division of application No. 13/469,027, filed on May 10, 2012, now Pat. No. 8,311,769, which is a division of application No. 13/246,843, filed on Sep. 27, 2011, now Pat. No. 8,180,591, which is a division of application No. 13/156,304, filed on Jun. 8, 2011, application No. 14/178,232, which is a continuation-in-part of application No. 13/959,714, which is a continuation-in-part of application No. 13/759,485, filed on Feb. 5, 2013, now Pat. No. 8,543,351, which is a division of application No. 13/667,229, which is a division of application No. 13/469,027, which is a division of application No. 13/246,843, which is a division of application No. 13/156,304, application No. 14/178,232, which is a continuation-in-part of application No. 13/959,714, application No. 14/178,232, which is a continuation of application No. 14/174,497, filed on Feb. 6, 2014.

(60) Provisional application No. 61/388,595, filed on Sep. 30, 2010, provisional application No. 61/390,811, filed on Oct. 7, 2010, provisional application No. 61/680,230, filed on Aug. 6, 2012, provisional application No. 61/762,210, filed on Feb. 7, 2013.

(51) Int. Cl.

| | |
|---|---|
| *G06F 19/00* | (2011.01) |
| *H04L 29/08* | (2006.01) |
| *G01C 22/00* | (2006.01) |
| *A63B 24/00* | (2006.01) |
| *A63B 71/06* | (2006.01) |
| *G06F 15/00* | (2006.01) |
| *A61B 5/11* | (2006.01) |
| *A61B 5/00* | (2006.01) |
| *A61B 5/22* | (2006.01) |
| *A61B 5/021* | (2006.01) |
| *A61B 5/0205* | (2006.01) |
| *A61B 5/024* | (2006.01) |

(52) U.S. Cl.
CPC ............... *H04L 67/22* (2013.01); *A61B 5/4809* (2013.01); *A63B 2220/72* (2013.01); *A63B 2230/50* (2013.01); *G01C 22/006* (2013.01); *A63B 24/0062* (2013.01); *G06F 19/3406* (2013.01); *A61B 5/4815* (2013.01); *A61B 5/4812* (2013.01); *A63B 2230/06* (2013.01); *A61B 5/222* (2013.01); *A61B 5/0022* (2013.01); *A61B 5/021* (2013.01); *A63B 71/0686* (2013.01); *G06F 15/00* (2013.01); *A61B 5/743* (2013.01); *A61B 2560/0242* (2013.01); *A61B 2560/0214* (2013.01); *G01C 22/00* (2013.01); *A63B 2230/75* (2013.01); *A61B 5/6838* (2013.01); *A61B 2562/0219* (2013.01); *G06F 19/3481* (2013.01); *A63B 2220/73* (2013.01); *A61B 5/1112* (2013.01); *A61B 5/744* (2013.01); *A61B 5/1118* (2013.01); *A61B 5/02055* (2013.01); *A61B 5/7264* (2013.01); *A61B 5/024* (2013.01); *A63B 2230/70* (2013.01)
USPC ........................................ 702/160

(58) Field of Classification Search
USPC ............ 702/160, 155, 182–185, 188
See application file for complete search history.

(56) References Cited

U.S. PATENT DOCUMENTS

| | | |
|---|---|---|
| 2,717,736 A | 9/1955 | Schlesinger |
| 2,883,255 A | 4/1959 | Anderson |
| 3,163,856 A | 12/1964 | Kirby |
| 3,250,270 A | 5/1966 | Bloom |
| 3,918,658 A | 11/1975 | Beller |
| 4,192,000 A | 3/1980 | Lipsey |
| 4,244,020 A | 1/1981 | Ratcliff |
| 2,284,849 A | 8/1981 | Anderson et al. |
| 4,281,663 A | 8/1981 | Pringle |
| 4,284,849 A | 8/1981 | Anderson et al. |
| 4,312,358 A | 1/1982 | Barney |
| 4,367,752 A | 1/1983 | Jimenez et al. |
| 4,390,922 A | 6/1983 | Pelliccia |
| 4,407,295 A | 10/1983 | Steuer et al. |
| 4,425,921 A | 1/1984 | Fujisaki et al. |
| 4,575,804 A | 3/1986 | Ratcliff |
| 4,578,769 A | 3/1986 | Frederick |
| 4,617,525 A | 10/1986 | Lloyd |
| 4,887,249 A | 12/1989 | Thinesen |
| 4,977,509 A | 12/1990 | Pitchford et al. |
| 5,058,427 A | 10/1991 | Brandt |
| 5,224,059 A | 6/1993 | Nita et al. |
| 5,295,085 A | 3/1994 | Hoffacker |
| 5,323,650 A | 6/1994 | Fullen et al. |
| 5,446,705 A | 8/1995 | Haas et al. |
| 5,456,648 A | 10/1995 | Edinburg et al. |
| 5,583,776 A | 12/1996 | Levi et al. |
| 5,671,162 A | 9/1997 | Werbin |
| 5,704,350 A | 1/1998 | Williams, III |
| 5,724,265 A | 3/1998 | Hutchings |
| 5,890,128 A | 3/1999 | Diaz et al. |
| 5,891,042 A | 4/1999 | Sham et al. |
| 5,894,454 A | 4/1999 | Kondo |
| 5,899,963 A | 5/1999 | Hutchings |
| 5,947,868 A | 9/1999 | Dugan |
| 5,955,667 A | 9/1999 | Fyfe |
| 5,976,083 A | 11/1999 | Richardson et al. |
| 6,018,705 A | 1/2000 | Gaudet et al. |
| 6,077,193 A | 6/2000 | Buhler et al. |
| 6,085,248 A | 7/2000 | Sambamurthy et al. |
| 6,129,686 A | 10/2000 | Friedman |
| 6,145,389 A | 11/2000 | Ebeling et al. |
| 6,183,425 B1 | 2/2001 | Whalen et al. |
| 6,213,872 B1 | 4/2001 | Harada et al. |
| 6,241,684 B1 | 6/2001 | Amino et al. |
| 6,287,262 B1 | 9/2001 | Amano et al. |
| 6,301,964 B1 | 10/2001 | Fyfe et al. |
| 6,302,789 B2 | 10/2001 | Harada et al. |
| 6,305,221 B1 | 10/2001 | Hutchings |
| 6,309,360 B1 | 10/2001 | Mault |
| 6,469,639 B2 | 10/2002 | Tanenhaus et al. |
| 6,478,736 B1 | 11/2002 | Mault |
| 6,513,381 B2 | 2/2003 | Fyfe et al. |
| 6,513,532 B2 | 2/2003 | Mault et al. |
| 6,527,711 B1 | 3/2003 | Stivoric et al. |
| 6,529,827 B1 | 3/2003 | Beason et al. |
| 6,561,951 B2 | 5/2003 | Cannon et al. |
| 6,571,200 B1 | 5/2003 | Mault |
| 6,585,622 B1 | 7/2003 | Shum et al. |
| 6,607,493 B2 | 8/2003 | Song |
| 6,620,078 B2 | 9/2003 | Pfeffer |
| 6,678,629 B2 | 1/2004 | Tsuji |
| 6,699,188 B2 | 3/2004 | Wessel |
| 6,761,064 B2 | 7/2004 | Tsuji |
| 6,790,178 B1 | 9/2004 | Mault et al. |
| 6,808,473 B2 | 10/2004 | Hisano et al. |
| 6,811,516 B1 | 11/2004 | Dugan |
| 6,813,582 B2 | 11/2004 | Levi et al. |
| 6,813,931 B2 | 11/2004 | Yadav et al. |
| 6,856,938 B2 | 2/2005 | Kurtz |
| 6,862,575 B1 | 3/2005 | Anttila et al. |
| 7,062,225 B2 | 6/2006 | White |
| 7,162,368 B2 | 1/2007 | Levi et al. |
| 7,171,331 B2 | 1/2007 | Vock et al. |
| 7,200,517 B2 | 4/2007 | Darley et al. |
| 7,246,033 B1 | 7/2007 | Kudo |
| 7,261,690 B2 | 8/2007 | Teller et al. |
| 7,272,982 B2 | 9/2007 | Neuhauser et al. |
| 7,373,820 B1 | 5/2008 | James |
| 7,443,292 B2 | 10/2008 | Jensen et al. |
| 7,457,724 B2 | 11/2008 | Vock et al. |
| 7,467,060 B2 | 12/2008 | Kulach et al. |
| 7,505,865 B2 | 3/2009 | Ohkubo et al. |
| 7,559,877 B2 | 7/2009 | Parks et al. |
| 7,653,508 B1 | 1/2010 | Kahn et al. |
| 7,690,556 B1 | 4/2010 | Kahn et al. |
| 7,713,173 B2 | 5/2010 | Shin et al. |
| 7,762,952 B2 | 7/2010 | Lee et al. |
| 7,774,156 B2 | 8/2010 | Niva et al. |
| 7,789,802 B2 | 9/2010 | Lee et al. |
| 7,881,902 B1 | 2/2011 | Kahn et al. |
| 7,927,253 B2 | 4/2011 | Vincent et al. |
| 7,983,876 B2 | 7/2011 | Vock et al. |
| 8,028,443 B2 | 10/2011 | Case, Jr. |
| 8,055,469 B2 | 11/2011 | Kulach et al. |
| 8,099,318 B2 | 1/2012 | Moukas et al. |
| 8,177,260 B2 | 5/2012 | Tropper et al. |
| 8,180,591 B2 | 5/2012 | Yuen et al. |
| 8,180,592 B2 | 5/2012 | Yuen et al. |
| 8,311,769 B2 | 11/2012 | Yuen et al. |
| 8,311,770 B2 | 11/2012 | Yuen et al. |
| 8,386,008 B2 | 2/2013 | Yuen et al. |
| 8,437,980 B2 | 5/2013 | Yuen et al. |
| 8,463,576 B2 | 6/2013 | Yuen et al. |
| 8,463,577 B2 | 6/2013 | Yuen et al. |
| 8,543,185 B2 | 9/2013 | Yuen et al. |
| 8,543,351 B2 | 9/2013 | Yuen et al. |
| 8,548,770 B2 | 10/2013 | Yuen et al. |
| 8,583,402 B2 | 11/2013 | Yuen et al. |
| 8,597,093 B2 | 12/2013 | Engelberg et al. |
| 8,670,953 B2 | 3/2014 | Yuen et al. |
| 2001/0055242 A1 | 12/2001 | Deshmukh et al. |
| 2002/0013717 A1 | 1/2002 | Ando et al. |
| 2002/0077219 A1 | 6/2002 | Cohen et al. |
| 2002/0082144 A1 | 6/2002 | Pfeffer |
| 2002/0109600 A1 | 8/2002 | Mault et al. |
| 2002/0178060 A1 | 11/2002 | Sheehan |
| 2002/0198776 A1 | 12/2002 | Nara et al. |
| 2003/0018523 A1 | 1/2003 | Rappaport et al. |
| 2003/0050537 A1 | 3/2003 | Wessel |
| 2003/0065561 A1 | 4/2003 | Brown et al. |
| 2003/0131059 A1 | 7/2003 | Brown et al. |
| 2004/0054497 A1 | 3/2004 | Kurtz |
| 2004/0061324 A1 | 4/2004 | Howard |
| 2004/0117963 A1 | 6/2004 | Schneider |
| 2004/0152957 A1 | 8/2004 | Stivoric et al. |
| 2005/0037844 A1 | 2/2005 | Shum et al. |
| 2005/0038679 A1 | 2/2005 | Short |
| 2005/0054938 A1 | 3/2005 | Wehman et al. |
| 2005/0102172 A1 | 5/2005 | Sirmans, Jr. |
| 2005/0107723 A1 | 5/2005 | Wehman et al. |
| 2005/0228244 A1 | 10/2005 | Banet |
| 2005/0228692 A1 | 10/2005 | Hodgdon |
| 2005/0234742 A1 | 10/2005 | Hodgdon |
| 2005/0248718 A1 | 11/2005 | Howell et al. |
| 2005/0272564 A1 | 12/2005 | Pyles et al. |
| 2006/0020177 A1 | 1/2006 | Seo et al. |
| 2006/0025282 A1 | 2/2006 | Redmann |
| 2006/0047208 A1 | 3/2006 | Yoon |
| 2006/0047447 A1 | 3/2006 | Brady et al. |
| 2006/0089542 A1 | 4/2006 | Sands |
| 2006/0111944 A1 | 5/2006 | Sirmans, Jr. et al. |
| 2006/0129436 A1 | 6/2006 | Short |
| 2006/0143645 A1 | 6/2006 | Vock et al. |
| 2006/0277474 A1 | 12/2006 | Robarts et al. |
| 2006/0282021 A1 | 12/2006 | DeVaul et al. |
| 2006/0287883 A1 | 12/2006 | Turgiss et al. |
| 2007/0050715 A1 | 3/2007 | Behar |
| 2007/0051369 A1 | 3/2007 | Choi et al. |
| 2007/0071643 A1 | 3/2007 | Hall et al. |
| 2007/0123391 A1 | 5/2007 | Shin et al. |
| 2007/0136093 A1 | 6/2007 | Rankin et al. |
| 2007/0155277 A1 | 7/2007 | Amitai et al. |
| 2007/0159926 A1 | 7/2007 | Prstojevich et al. |

| | | |
|---|---|---|
| 2007/0179356 A1 | 8/2007 | Wessel |
| 2007/0194066 A1 | 8/2007 | Ishihara et al. |
| 2007/0197920 A1 | 8/2007 | Adams |
| 2007/0208544 A1 | 9/2007 | Kulach et al. |
| 2007/0276271 A1 | 11/2007 | Chan |
| 2008/0093838 A1 | 4/2008 | Tropper et al. |
| 2008/0125288 A1 | 5/2008 | Case |
| 2008/0140163 A1 | 6/2008 | Keacher et al. |
| 2008/0140338 A1 | 6/2008 | No et al. |
| 2009/0018797 A1 | 1/2009 | Kasama et al. |
| 2009/0043531 A1 | 2/2009 | Kahn et al. |
| 2009/0048044 A1 | 2/2009 | Oleson et al. |
| 2009/0054737 A1* | 2/2009 | Magar et al. .................. 600/300 |
| 2009/0063193 A1 | 3/2009 | Barton et al. |
| 2009/0171788 A1 | 7/2009 | Tropper et al. |
| 2009/0271147 A1 | 10/2009 | Sugai |
| 2010/0205541 A1 | 8/2010 | Rapaport et al. |
| 2010/0217099 A1 | 8/2010 | LeBoeuf et al. |
| 2011/0003665 A1 | 1/2011 | Burton et al. |
| 2011/0009051 A1 | 1/2011 | Khedouri et al. |
| 2011/0022349 A1 | 1/2011 | Stirling et al. |
| 2011/0080349 A1 | 4/2011 | Holbein et al. |
| 2011/0106449 A1 | 5/2011 | Chowdhary et al. |
| 2011/0131005 A1 | 6/2011 | Ueshima et al. |
| 2011/0193704 A1 | 8/2011 | Harper et al. |
| 2011/0224508 A1 | 9/2011 | Moon |
| 2011/0230729 A1 | 9/2011 | Shirasaki et al. |
| 2012/0072165 A1 | 3/2012 | Jallon |
| 2012/0083705 A1 | 4/2012 | Yuen et al. |
| 2012/0083714 A1 | 4/2012 | Yuen et al. |
| 2012/0083715 A1 | 4/2012 | Yuen et al. |
| 2012/0083716 A1 | 4/2012 | Yuen et al. |
| 2012/0084053 A1 | 4/2012 | Yuen et al. |
| 2012/0084054 A1 | 4/2012 | Yuen et al. |
| 2012/0092157 A1 | 4/2012 | Tran |
| 2012/0183939 A1 | 7/2012 | Aragones et al. |
| 2012/0226471 A1 | 9/2012 | Yuen et al. |
| 2012/0226472 A1 | 9/2012 | Yuen et al. |
| 2012/0227737 A1 | 9/2012 | Mastrototaro et al. |
| 2012/0265480 A1 | 10/2012 | Oshima |
| 2012/0330109 A1 | 12/2012 | Tran |
| 2013/0006718 A1 | 1/2013 | Nielsen et al. |
| 2013/0072169 A1 | 3/2013 | Ross et al. |
| 2013/0073254 A1 | 3/2013 | Yuen et al. |
| 2013/0073255 A1 | 3/2013 | Yuen et al. |
| 2013/0080113 A1 | 3/2013 | Yuen et al. |
| 2013/0095459 A1 | 4/2013 | Tran |
| 2013/0096843 A1 | 4/2013 | Yuen et al. |
| 2013/0151196 A1 | 6/2013 | Yuen et al. |
| 2013/0158369 A1 | 6/2013 | Yuen et al. |
| 2013/0231574 A1 | 9/2013 | Tran |
| 2013/0261475 A1 | 10/2013 | Mochizuki |
| 2013/0267249 A1 | 10/2013 | Rosenberg, David |
| 2013/0268199 A1 | 10/2013 | Nielsen et al. |
| 2013/0268236 A1 | 10/2013 | Yuen et al. |
| 2013/0296666 A1 | 11/2013 | Kumar et al. |
| 2013/0296673 A1 | 11/2013 | Thaveeprungsriporn et al. |
| 2013/0310896 A1 | 11/2013 | Mass |
| 2013/0325396 A1 | 12/2013 | Yuen et al. |
| 2014/0035761 A1 | 2/2014 | Burton et al. |
| 2014/0039804 A1 | 2/2014 | Park et al. |
| 2014/0039840 A1 | 2/2014 | Yuen et al. |
| 2014/0077673 A1 | 3/2014 | Garg et al. |

FOREIGN PATENT DOCUMENTS

| | | |
|---|---|---|
| JP | 11347021 | 12/1999 |
| WO | WO 2008/038141 | 4/2008 |
| WO | WO 2009/042965 | 4/2009 |

OTHER PUBLICATIONS

"Automatic classification of ambulatory movements and evaluation of energy consumptions utilizing accelerometers and barometer", Ohtaki, et al, Microsystem Technologies, vol. 11, No. 8-10, Aug. 2005, pp. 1034-1040.

"Classification of Human Moving Patterns Using Air Pressure and Acceleration", Sagawa, et al, Proceedings of the 24th Annual Conference of the IEEE Industrial Electronics Society, vol. 2, Aug.-Sep. 1998, pp. 1214-1219.

"Non-restricted measurement of walking distance", Sagawa, et al, IEEE Int' 1 Conf. on Systems, Man, and Cybernetics, vol. 3, Oct. 2000, pp. 1847-1852.

"Activity Classification Using Realistic Data From Wearable Sensors", Parkka, et al, IEEE Transactions on Information Technology in Biomedicine, vol. 10, No. 1, Jan. 2006, pp. 119-128.

"Indoor Navigation with MEMS Sensors", Lammel, et al., Proceedings of the Eurosensors XIII conference, vol. 1, No. 1, Sep. 2009, pp. 532-535.

"Design of a Wireless Assisted Pedestrian Dead Reckoning System—The NavMote Experience", Fang, et al, IEEE Transactions on Instrumentation and Measurement, vol. 54, No. 6, Dec. 2005, pp. 2342-2358.

"On Foot Navigation: When GPS alone is not Enough", Ladetto, et al, Journal of Navigation, vol. 53, No. 2, Sep. 2000, pp. 279-285.

"A Hybrid Discriminative/Generative Approach for Modeling Human Activities", Lester, et al., Proc. of the Int'l Joint Conf. Artificial Intelligence, 2005, pp. 766-772.

"Using MS5534 for altimeters and barometers", Intersema App., Note AN501, Jan. 2006.

"Validated caloric expenditure estimation using a single body-worn sensor", Lester, et al, Proc. of the Int'l Conf. on Ubiquitous Computing, 2009, pp. 225-234.

"Drift-free dynamic height sensor using MEMS IMU aided by MEMS pressure sensor", Tanigawa, et al, Workshop on Positioning, Navigation and Communication, Mar. 2008, pp. 191-196.

"Improvement of Walking Speed Prediction by Accelerometry and Altimetry, Validated by Satellite Positioning", Perrin, et al, Medical & Biological Engineering & Computing, vol. 38, 2000, pp. 164-168.

"An Intelligent Multi-Sensor system for Pedestrian Navigation", Retscher, Journal of Global Positioning Systems, vol. 5, No. 1, 2006, pp. 110-118.

"Evaluation of a New Method of Heading Estimation of Pedestrian Dead Reckoning Using Shoe Mounted Sensors", Stirling et al., Journal of Navigation, vol. 58, 2005, pp. 31-45.

"Direct Measurement of Human Movement by Accelerometry", Godfrey, et al., Medical Engineering & Physics, vol. 30, 2008, pp. 1364-1386.

"Foot Mounted Inertia System for Pedestrian Naviation", Godha et al., Measurement Science and Technology, vol. 19, No. 7, May 2008, pp. 1-9.

"Altimeter and Barometer System", Clifford, et al., Freescale Semiconductor Aplication Note AN1979, Rev. 3, Nov. 2006.

"SCP 1000-D01/D11 Pressure Sensor as Barometer and Altimeter", VTI Technologies Application, Jun. 2006, Note 33.

"Suunto LUMI User Guide", Jun. and Sep. 1997.

International Search Report issued on Aug. 15, 2008, in related application PCT/IB07/03617.

Deepak et al., Plug-and-Play, Single-Chip Photoplethysmography, 34th Annual International Conference of the IEEE EMBS, San Diego, California USA, Aug. 28-Sep. 1, 2012, 4 pages.

* cited by examiner

*Primary Examiner* — Edward Raymond

(74) *Attorney, Agent, or Firm* — Martine Penilla Group, LLP

(57) ABSTRACT

Methods, devices, and computer programs are presented for creating a unified data stream from multiple data streams acquired from multiple devices. One method includes an operation for receiving activity data streams from the devices, each activity data stream being associated with physical activity data of a user. Further, the method includes an operation for assembling the unified activity data stream for a period of time. The unified activity data stream includes data segments from the data streams of at least two devices, and the data segments are organized time-wise over the period of time.

27 Claims, 17 Drawing Sheets

Rules database

| id | Trigger | Action |
|---|---|---|
| 1 | Running | Select Device A |
| 2 | Sleeping | Select Device B |
| 3 | Climbing steps | Average (A, C) |
| 4 | At Office | Select Device D |
| 5 | At the gym | Maximum (C, F, G) |
| 6 | At home | Minimum (All active devices) |
| 7 | Driving | Use Car GPS |
| ... | | |

TRACKING USER PHYSICAL ACTIVITY WITH MULTIPLE DEVICES

CLAIM OF PRIORITY

This application is a Continuation application under 35 USC §120 of U.S. application Ser. No. 14/174,497, entitled "Method of Data Synthesis", and filed on Feb. 6, 2014, which claims priority from U.S. Provisional Patent Application No. 61/762,210, filed Feb. 7, 2013, and entitled "Method of Data Synthesis," all of which are herein incorporated by reference.

This application is a continuation-in-part of U.S. patent application Ser. No. 13/959,714, filed on Aug. 5, 2013, titled "Methods and Systems for Identification of Event Data Having Combined Activity and Location Information of Portable Monitoring Devices", which is a continuation-in-part of U.S. patent application Ser. No. 13/693,334 (now issued as U.S. Pat. No. 8,548,770, issued on Oct. 1, 2013), filed on Dec. 4, 2012, titled "Portable Monitoring Devices and Methods for Operating Same", which is a divisional of U.S. patent application Ser. No. 13/667,229 (now issued as U.S. Pat. No. 8,437,980, issued on May 7, 2013), filed on Nov. 2, 2012, titled "Portable Monitoring Devices and Methods for Operating Same", which is a divisional of U.S. patent application Ser. No. 13/469,027, now U.S. Pat. No. 8,311,769, filed on May 10, 2012, titled "Portable Monitoring Devices and Methods for Operating Same", which is a divisional of U.S. patent application Ser. No. 13/246,843, now U.S. Pat. No. 8,180,591, filed on Sep. 27, 2011, which is a divisional of U.S. patent application Ser. No. 13/156,304, filed on Jun. 8, 2011, titled "Portable Monitoring Devices and Methods for Operating Same", which claims the benefit of and priority to, under 35 U.S.C. 119§(e), to U.S. Provisional Patent Application No. 61/388,595, filed on Sep. 30, 2010, and titled "Portable Monitoring Devices and Methods for Operating Same", and to U.S. Provisional Patent Application No. 61/390,811, filed on Oct. 7, 2010, and titled "Portable Monitoring Devices and Methods for Operating Same", all of which are hereby incorporated by reference in their entirety.

This application is a continuation-in-part of Ser. No. 13/959,714, filed Aug. 5, 2013, titled "Methods and Systems for Identification of Event Data Having Combined Activity and Location Information of Portable Monitoring Devices", which claims priority to U.S. Provisional Patent Application 61/680,230 filed Aug. 6, 2012, and is a continuation-in-part of U.S. patent application Ser. No. 13/759,485 (now issued as U.S. Pat. No. 8,543,351, issued on Sep. 24, 2013), filed on Feb. 5, 2013, titled "Portable Monitoring Devices and Methods for Operating Same", which is a divisional of U.S. patent application Ser. No. 13/667,229, filed on Nov. 2, 2012, titled "Portable Monitoring Devices and Methods for Operating Same" (now issued as U.S. Pat. No. 8,543,351, issued on May 7, 2013), which is a divisional of U.S. patent application Ser. No. 13/469,027, now U.S. Pat. No. 8,311,769, filed on May 10, 2012, titled "Portable Monitoring Devices and Methods for Operating Same", which is a divisional of U.S. patent application Ser. No. 13/246,843, now U.S. Pat. No. 8,180,591, filed on Sep. 27, 2011, which is a divisional of U.S. patent application Ser. No. 13/156,304, filed on Jun. 8, 2011, titled "Portable Monitoring Devices and Methods for Operating Same", which claims the benefit of and priority to, under 35 U.S.C. 119§(e), to U.S. Provisional Patent Application No. 61/388,595, filed on Sep. 30, 2010, and titled "Portable Monitoring Devices and Methods for Operating Same" and to U.S. Provisional Patent Application No. 61/390,811, filed on Oct. 7, 2010, and titled "Portable Monitoring Devices and Methods for Operating Same", all of which are hereby incorporated by reference in their entirety.

CROSS REFERENCE TO RELATED APPLICATIONS

This application is related by subject matter to U.S. patent application Ser. No. 14/178,224 filed on the same day as the instant application and entitled "Method of Data Synthesis", which is incorporated herein by reference.

BACKGROUND

1. Field of the Invention

The present embodiments relate to methods, devices, systems, and computer programs for analyzing data, and more particularly, methods, devices, systems, and computer programs for consolidating overlapping data provided by multiple devices.

2. Description of the Related Art

The use of portable devices has grown exponentially over the last few decades, and in particularly, the use of biometric monitoring devices that users wear on their bodies to measure activity levels, as well measuring environmental or user parameters (e.g., temperature, heart rate, altitude, etc.). Sometimes, data related to user activities may be acquired from multiple devices, such as a pedometer, a smart phone, a GPS (Global Positioning System) device, a thermometer, a weight scale, etc.

Occasionally, two or more devices can provide information about the same parameter related to activities of the user. For example, a user may get a step count from a pedometer worn on the wrist and from a step counter embedded on a running shoe. However, the accuracy of the different devices may change according to the inherent accuracy of the device or according to environmental circumstances (e.g., poor GPS satellite data reception).

When the user gets conflicting information from multiple devices, the user may not know which is the accurate data. A system is desired to identify the best source of information in order to provide the best possible data to the user.

It is in this context that embodiments arise.

SUMMARY

Methods, devices, systems, and computer programs are presented for consolidating overlapping data provided by multiple sources. It should be appreciated that the present embodiments can be implemented in numerous ways, such as a method, an apparatus, a system, a device, or a computer program on a computer readable medium. Several embodiments are described below.

The present embodiments relate to methods, systems, and computer programs for combining or synthesizing multiple data streams into a unified data stream while maintaining accuracy and integrity of the data. In an embodiment, the data includes environmental and biometric data. In another embodiment, the multiple data streams originate from, or are collected by, multiple devices that monitor the same or similar physical phenomena. For example, one embodiment includes a method used by a cloud-based activity-monitoring server to combine data streams from multiple portable biometric monitoring devices tracking a single user or group of users. In another embodiment, the method pertains to a device (e.g., personal computer, tablet computer, smartphone) that combines data streams from multiple portable biometric monitoring devices tracking a single user or a group of users.

In one embodiment, a method includes operations for receiving a plurality of activity data streams from a plurality of devices, each activity data stream being associated with physical activity data of a user. In addition, the method includes an operation for assembling a unified activity data stream for the user over a period of time, the unified activity data stream including data segments from the data streams of at least two devices of the plurality of devices, and the data segments being organized time-wise over the period of time. In one embodiment, the operations of the method are executed by a processor.

In another embodiment, a server includes a communications module, a memory, and a processor. The communications module is operable to receive a plurality of activity data streams from a plurality of devices, each activity data stream being associated with physical activity data of a user. Further, the memory is operable to store the plurality of activity data streams and a unified activity data stream that includes data segments from the data streams of at least two devices of the plurality of devices. In addition, the processor is operable to assemble the unified activity data stream for the user over a period of time. The data segments are organized time-wise over the period of time.

In another embodiment, a non-transitory computer-readable storage medium storing a computer program is provided. The computer-readable storage medium includes program instructions for receiving a plurality of activity data streams from a plurality of devices, each activity data stream being associated with physical activity data of a user. Further, the storage medium includes program instructions for assembling a unified activity data stream for the user over a period of time, the unified activity data stream including data segments from the data streams of at least two devices of the plurality of devices, the data segments being organized time-wise over the period of time.

In yet another embodiment, one method includes operations for receiving data streams regarding activity of a user, each data stream being associated with a respective device of a plurality of devices, and for evaluating one or more rules for consolidating the data streams into a unified activity data stream. Evaluating the one or more rules further includes identifying first time segments where data is available from a single device from the plurality of devices; adding the available data to the unified activity data stream for the first time segments; identifying second time segments where data exists from two or more devices from the plurality of devices; and adding data to the second time segments based on the existing data from the two or more devices and based on the one or more rules. Further, the method includes an operation for storing the unified activity data stream for presentation to the user. In one embodiment, the operations of the method are executed by a processor.

Other aspects will become apparent from the following detailed description, taken in conjunction with the accompanying drawings.

BRIEF DESCRIPTION OF THE DRAWINGS

The embodiments may best be understood by reference to the following description taken in conjunction with the accompanying drawings.

DETAILED DESCRIPTION

Methods, devices, systems, and computer programs are presented for consolidating overlapping data provided by multiple devices. It will be apparent, that the present embodiments may be practiced without some or all of these specific details. In other instances, well-known process operations have not been described in detail in order not to unnecessarily obscure the present embodiments.

Figure 1:
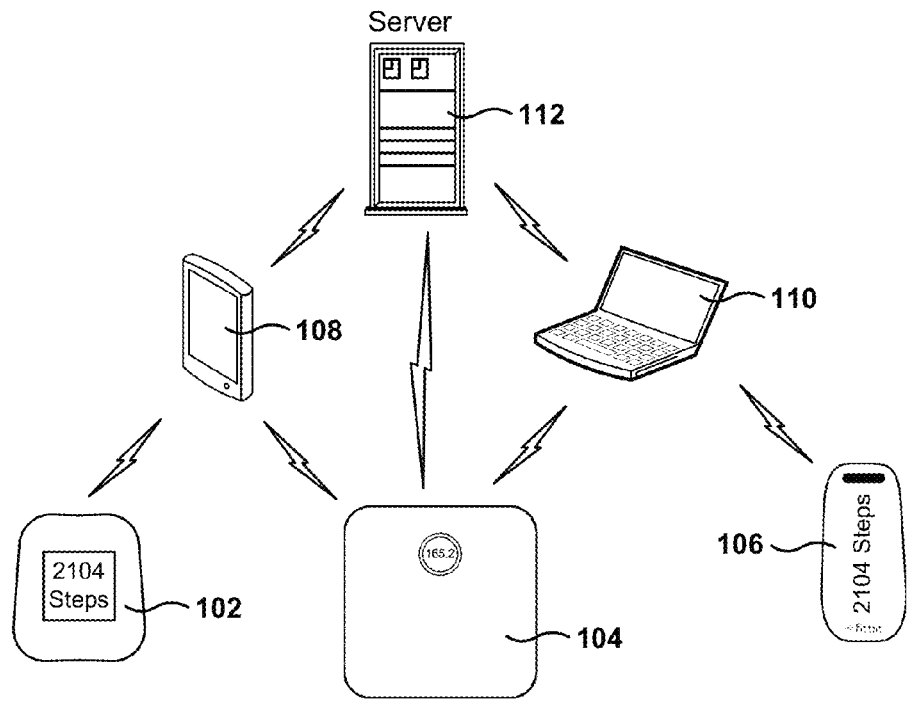
FIG. 1 is a block diagram of a system architecture according to one embodiment.

FIG. 1 is a block diagram of a system architecture according to one embodiment. Portable biometric devices will be referred to herein by way of example to illustrate aspects of the invention. The embodiments are not limited to portable biometric devices, however, as the data synthesis of multiple data sources may be applied to any type of data.

Some biometric monitoring devices are portable and have shapes and sizes that are adapted to couple to the body of a user (e.g., a pedometers 102, 106), while other devices are carried by the user (e.g., mobile phone 108, laptop 110, tablet), and other devices may be stationary (e.g., electronic scale 104, a digital thermometer, personal computer).

The devices collect one or more types of physiological or environmental data from embedded sensors or external devices. The devices can then communicate the data to other devices, to one or more servers 112, or to other internet-viewable sources. As one example, while the user is wearing a biometric monitoring device 102, the device can calculate and store the number of steps taken by the user (the user's step count) from data collected by embedded sensors. Data representing the user's step count is then transmitted to an account on a web service (such as www.fitbit.com, for example) where the data may be stored, processed, and viewed by the user. Indeed, the device may measure or calculate a plurality of other physiological metrics in addition to, or in place of, the user's step count.

These metrics include, but are not limited to, energy expenditure (e.g., calorie burn), floors climbed or descended, heart rate, heart rate variability, heart rate recovery, location and/or heading (e.g., through GPS), elevation, ambulatory speed and/or distance traveled, swimming lap count, bicycle distance and/or speed, blood pressure, blood glucose, skin conduction, skin and/or body temperature, electromyography, electroencephalography, weight, body fat, caloric intake, nutritional intake from food, medication intake, sleep periods (i.e., clock time), sleep phases, sleep quality, and/or sleep duration, and respiration rate. The device may also measure or calculate metrics related to the environment around the user such as barometric pressure, weather conditions (e.g., temperature, humidity, pollen count, air quality, rain/snow conditions, wind speed), light exposure (e.g., ambient light, UV light exposure, time and/or duration spent in darkness), noise exposure, radiation exposure, and magnetic field.

As used herein, the term "sync" refers to the action of exchanging data between a first device and a second device to update the second device with new information available to the first device that is not yet available to the second device. Additionally, "sync" may also referred to the exchange of information between two devices to provide updates to one of the devices with information available to the other device, or to coordinate information that is available, overlapping, or redundant in both devices. "Sync" may also be used in reference to sending and/or receiving data to and/or from another computing device or electronic storage devices including, but not limited to, a personal computer, a cloud based server, and a database. In some embodiments, a sync from one electronic device to another may occur through the use of one or more intermediary electronic devices. For example, data from a personal biometric device may be transmitted to a smart phone that forwards the data to a server.

Furthermore, a device or system combining multiple data streams may calculate metrics derived from this data. For example, the device or system can calculate the user's stress levels and the risk level of elevated stress, through one or more of heart rate variability, skin conduction, noise pollution, and sleep quality. Conversely, the device or system may calculate the user's stress reduction (e.g., calmness), or the stress reduction risk through one or more of the preceding parameters. In another embodiment, the device or system may determine the efficacy of a medical intervention (e.g., medication) through the combination of medication intake, sleep data, and/or activity data. In yet another example, the device or system may determine the efficacy of an allergy medication through the combination of pollen data, medication intake, sleep data and/or activity data. These examples are provided for illustration and not to be interpreted to be exclusive or limiting.

The user may employ more than one portable monitoring device. For a case in which the user tracks the same class of data during the same period of time with more than one device, the two resulting data streams are combined or synthesized as described more fully below according to several embodiments.

"Class of data" or "data class" refers to data that represents a quantifiable characteristic or a set of quantifiable characteristics in one or more ways. For example, one data class may be ambulatory steps count. "Data type" refers to a specific representation of a quantifiable characteristic. Examples of data types may include walking steps per minute and running steps per minute. It is noted that both walking steps per minute and running steps per minute may be considered a part of the data class ambulatory step count.

Figure 2:
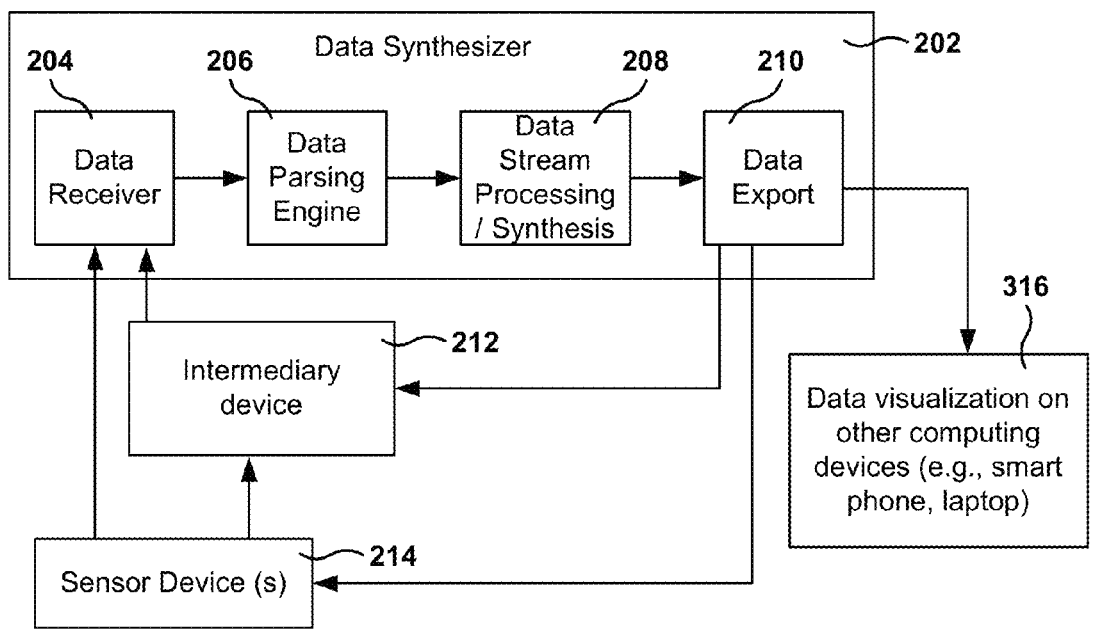
FIG. 2 is a block diagram of a data synthesizer according to one embodiment.

FIG. 2 is a block diagram of a data synthesizer according to one embodiment. Depending on the activity, a user may prefer information from one device over the information from another device. For example, if the user is walking the user may prefer the information from the step counter, and if the user is swimming the user may prefer the information from the GPS tracker. Sometimes, the user may prefer the GPS information from the mobile phone instead of the GPS information from a fitness monitoring device. The process by which information from multiple devices is combined or filtered is referred to herein as data synthesis.

In the context of this disclosure, the term data synthesis or data stream synthesis is used to describe the combination of multiple data streams into a single data stream or set of data streams using an algorithm or a set of algorithms. The use of the term "combination" does not imply that there are less data streams after data synthesis, in some cases the number of data streams inputted into a data synthesis system or algorithm may be more or may be less than the number of data streams outputted. Data synthesis may be performed on a central device (e.g., a smartphone, a biometric hub such as an activity watch, a personal computer, a tablet computer, a home gaming console, a household sensor (e.g., thermostat)), through a web-based portal (e.g., www.fitbit.com), or via a combination of a central device and a web-based portal. Any and all aspects of distributed computing, remote data storage, virtual memory, and cloud computing can be used for data synthesis in various embodiments.

In the context of this disclosure the term data synthesizer will be used to describe a computing device that is configured to accept data from two or more devices and to combine their data into a single data set, or to generate an aggregate metric from similar or corresponding metrics from respective devices.

In one embodiment, the data synthesizer 202 includes data receiver 204, data parsing engine 206, data stream processing/synthesis module 208, and data export module 210. The data receiver 204 receives information from sensor devices 214 or from other intermediary devices 212. An intermediary device 212 is a device that receives data from one entity and forwards the data to another entity. In one embodiment, the intermediary device 212 is a mobile phone, but other embodiments may utilize other types of devices capable of sending and receiving data. A sensor device 214 is any device able to capture user related information regarding user activities, user biometric measurements, or user environmental parameters.

Data parsing engine 206 receives a stream of data and analyzes the stream of data to identify data types and data values. More details are provided below with reference to FIGS. 3-5 regarding embodiments of several parsing engines, also referred to as parsers.

Data stream processing/synthesis module 208 analyzes multiple streams of data and utilizes different algorithms and rules for performing data synthesis on the multiple data streams. The output from the data stream processing/synthesis module 208 is passed to a data export module 210 that is able to transfer the synthesized data to all other modules or other devices. For example, in one embodiment, data export module 210 transfers the data to a computing device 216 for visualization of the data for presentation to the user. For example, the data may be visualized on a laptop or a smart phone.

It is noted that the embodiments illustrated in FIG. 2 are exemplary. Other embodiments may utilize different modules for data synthesis, or combine the functionality of several modules into a single module. The embodiments illustrated in FIG. 2 should therefore not be interpreted to be exclusive or limiting, but rather exemplary or illustrative.

Figure 3:
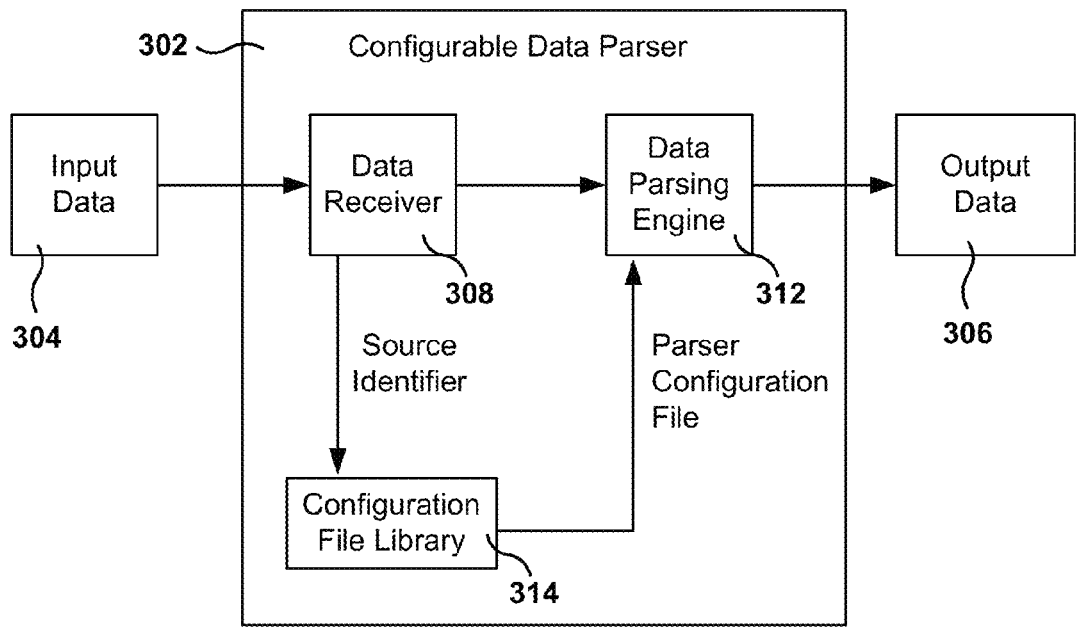
FIG. 3 is a block diagram of a data parser according to one embodiment.

FIG. 3 is a block diagram of a data parser according to one embodiment. The data synthesizer may use one or more methodologies to facilitate data input from sensor devices and other sources including, but not limited to, third party devices and third party food logging websites (e.g., MyFitnessPal). These methodologies allow the data synthesizer to determine which data streams represent the same type of information, regardless of the data stream source.

In one embodiment, a configurable data parsing engine 302, also referred to herein as configurable data parser, is used to accept input data 304 from multiple sources. The configurable data parser 302 includes a data receiver 308, a data parsing engine 312, and a configuration file library 314. The data receiver 308 handles communications with other devices to receive input data 304. Further, the configuration file library 314 includes files used to configure the data parsing engine 312, also referred to simply as the parser. When the source sends data to the data synthesizer, the parser is properly configured to read data from that specific source using the appropriate configuration file. The proper configuration file may be selected based on characteristics of the data stream source including, but not limited to, the device model, device identity, and/or an identifier in the data stream itself.

Figure 4:
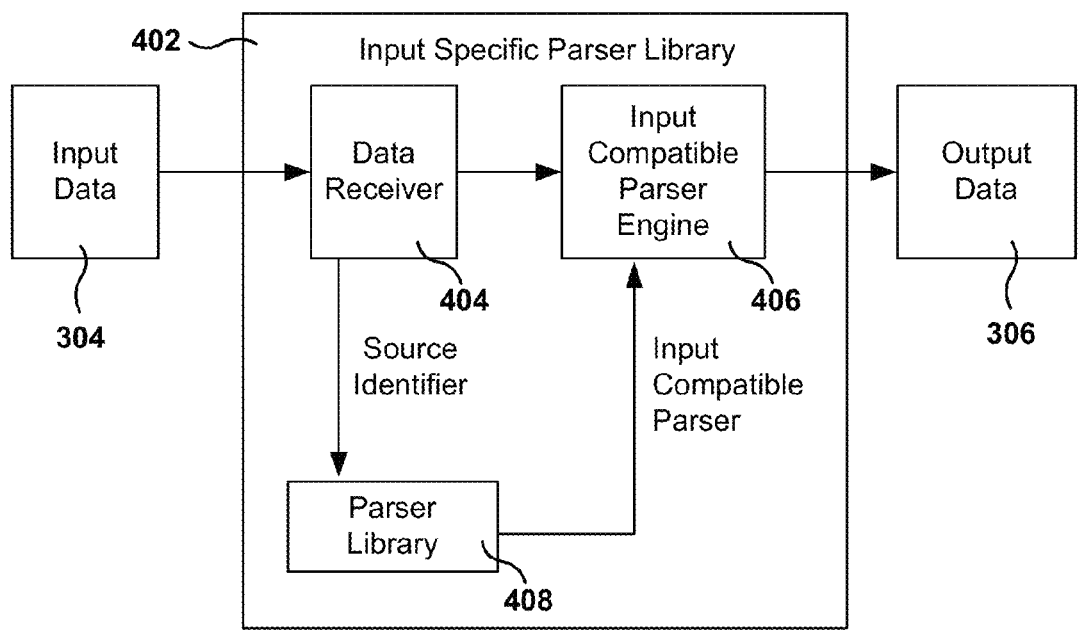
FIG. 4 is a block diagram of an input specific parser library according to one embodiment.

FIG. 4 is a block diagram of an input specific parser library according to one embodiment. In another embodiment, the data synthesizer may use a library of parsers to facilitate data input from sensor devices and other sources. The proper parser may be selected based on characteristics of the data stream source including but not limited to the device model, device identity, or an identifier in the data stream.

The input specific parser library 402 includes data receiver 404, input compatible parser engine 406, and parser library 408. The input compatible parser engine 406 selects one of the parsers from the parser library 408 in order to parse a specific data stream being provided as input data 304. Once the data is parsed with a specific parser, the output is provided as output data 306.

Figure 5:
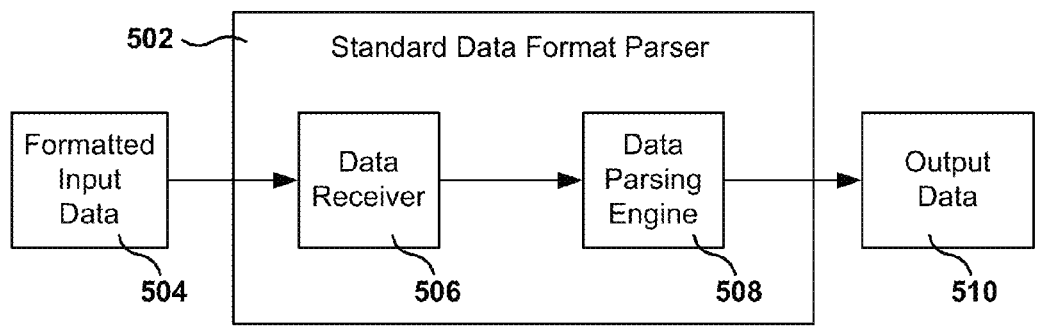
FIG. 5 is a block diagram of a standard data format parser according to one embodiment.

FIG. 5 is a block diagram of a standard data format parser according to one embodiment. In the embodiment of FIG. 5, each data source adheres to a standard data format, enabling the data synthesizer 502 to use a single data parser 508 for all data sources. A standard data format, or set of standard data formats, may be used with a configurable parser or library of parsers as well. For example, the data synthesizer may have a library of configuration files for a configurable data parser which includes configuration files for each data source class. Data source classes may include, but are not limited to, pedometer, scale, sleep tracker, online data entry, etc. Each of these classes may have a standard data format which can be read by a parser using the appropriate data source class configuration file. Formats such as XML and JSON may provide the framework for a standard data format, in some embodiments.

Some standard data formats require the data stream to specify the frequency of the data measurements or "sampling frequency." Depending on the data type and the device that is recording the data, a data point may represent a short or long period of time. For example, heart rate is a data type that is sampled at a high enough rate to measure heart rate variability. In one embodiment, the device recording heart rate data includes a monitor with a sampling rate of tens of hertz. As a contrasting example, blood glucose level and blood pressure are data types measured with a frequency of minutes to months.

The spectrum of sampling frequencies may be separated into two main bins. One bin is defined for any data that is typically sampled with a frequency on the order of daily or higher; data measured with this relatively low frequency sampling rate is referred to herein as "discrete" data. A second bin is defined for any data that is typically sampled with a frequency on the order of once per minute or shorter; data measured with this relatively high frequency sampling rate is referred to herein as "continuous" data. Continuous data may be acquired continuously (24/7), or for shorter periods of time, including but not limited to, 8 hours out of the day during week days. In other embodiments, data is separated into more than two bins based on its sampling frequency. Indeed, the data may be separated into an almost unlimited number of bins where the bin of a data type is defined by its sampling frequency.

The use of sampling frequency here refers to the frequency of derived data points, not the frequency of the raw sampling data. For example, a device using bioelectrical impedance analysis (BIA) may measure the impedance of a user with a sampling rate of 10 Hz and then analyze this data to create a single body fat measurement, as is done by a weight scale and body composition monitor, for instance. The sampling frequency of this data in this context would be the frequency with which body fat measurements were taken, not the raw BIA measurement rate.

In other cases these two rates may be equal. Other cases where the frequency of derived data points differs from that of the raw sampling data may also include data acquired over a period of time or activity in order to create a representative measurement of the whole period of time or activity. For example, an EKG strap may take many heart rate measurements during a run. At the end of the run, all of these measurements may be used to derive one or more metrics of the user's heart rate during the run including but not limited to the average heart rate, minimum heart rate, maximum heart rate, and maximum heart rate acceleration. In another example a GPS device may record a set of time stamped locations during a run. These locations may be used to derive the length of the run and the user's average speed.

An example of a continuous data type is a data stream for the distance walked in a minute. In a standard data format, this data type may have a specific name, for example "Walk_Speed." A standard data format may also require a standard unit. In the case of this example, feet per minute is an applicable standard measurement unit. The data type may also define the period over which the measurement is sampled, in this case one minute.

A standard data format may also require a timestamp. For example, each item of data logged may be assigned a timestamp of the form Year.Month.Day.Hour.Minute.Second. The standard data format may include other fields including, but not limited to, device manufacturer, device age, device accuracy, device precision, device model, and the location where the device is located or worn (wrist, shoe, belt, pocket, etc.).

Table 1 below provides examples of data types that can be recorded or operated on by the data synthesizer, portable biometric devices, and any intermediary computing devices (such as clients). While the data types are classified into biometric, environmental, continuous, and discrete categories, any data listed may be used in any of the listed categories. For example blood glucose is commonly measured 1-3 times a day in a discrete manner using test strips. Blood glucose may also be monitored continuously with a continuous blood glucose monitor. Many other data types not listed here may be used by the embodiments, and the listing here is not intended to be exhaustive or limiting.

TABLE 1

DATA TYPES

| Biometric | | Environmental | |
|---|---|---|---|
| Continuous | Discrete | Continuous | Discrete |
| steps | weight | location | Raining |
| elevation gained | BMI | elevation | Snowing |
| floors gained | BMR | temperature | |
| calories burned | distance traveled | indoor vs | |
| speed | SpO2 | outdoor | |
| velocity | blood pressure | watching TV | |
| heart rate | arterial stiffness | UV exposure | |
| heart rate while asleep | blood glucose levels | Ambient noise Air quality | |
| heart rate while sedentary | blood volume heart rate recovery | | |
| heart rate variability | time fall event | | |
| respiration rate | shower detection | | |
| SpO2 | sleep apnea detection | | |
| stress | cardiac arrhythmia | | |
| activity level detection | cardiac arrest pulse transit time | | |
| sitting/standing detection | Distance of an activity | | |
| muscle tension | Distance of a run | | |
| blood flow | Distance of a walk | | |
| laugh detection | Distance of a bike | | |
| respiration type- (snoring, breathing) | ride Distance of a swim | | |
| breathing problems | Duration of an | | |
| user's voice | activity | | |
| swimming detection | Duration of a run | | |
| heat flux | Duration of a walk | | |
| sleep phase detection | Duration of a bike ride | | |
| typing detection | Duration of a swim | | |
| | Duration of a workout | | |
| | Resting heart rate | | |
| | Maximum heart rate | | |
| | Active heart rate | | |
| | Hydration (extra cellular water) | | |
| | Muscle mass | | |
| | Body fat mass | | |

Methodologies for parsing input data streams, as described herein, may be used to feed back output data or device configurations from the data synthesizer to sensor devices or other services or computing devices. For example, the data synthesizer may use an unparser or serializer to format a data package to be sent back to a sensor device. This data package may contain updated user statistics such as step count, notifications for the user (e.g., new message, goal met, friend request), and device configuration updates (e.g., newly calibrated stride length).

In various embodiments, data from third parties is accepted (read and processed) by the data synthesizer. In this context, third party refers to a company or individual which is independent of the company or individual that manages and/or created the data synthesizer. For example, the company Fitbit may manage the data synthesizer and accept data from a third party company's devices or services such as MyFitnessPal™ or Garmin™. In one embodiment, third party data streams are accepted if the data streams meet a set of requirements to ensure that the third party data is reliable and properly handled. These requirements include adherence to a standardized data structure and identification format. Other requirements may include, but are not limited to, the data stream coming from a reputable or verified source, a certain level of accuracy, precision, and/or frequency in the measurement of data. In an embodiment, another requirement is the explicit consent of the user to allow the third party data to be combined with their existing data streams.

Figure 6:
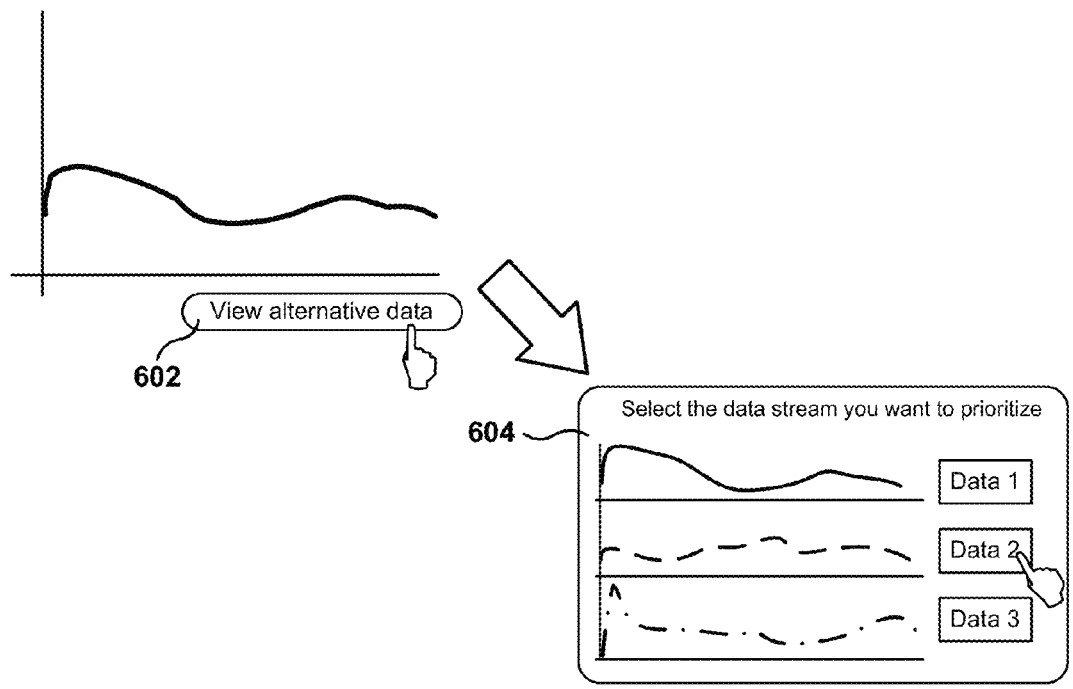
FIGS. 6-8 are diagrams of user interface screens according to several embodiments.
Figure 7:
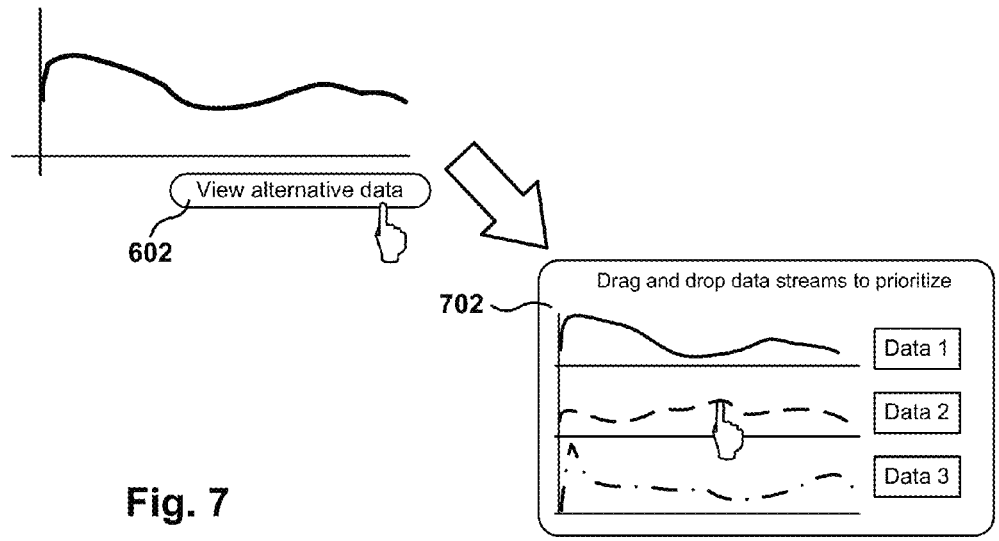
Figure 8:
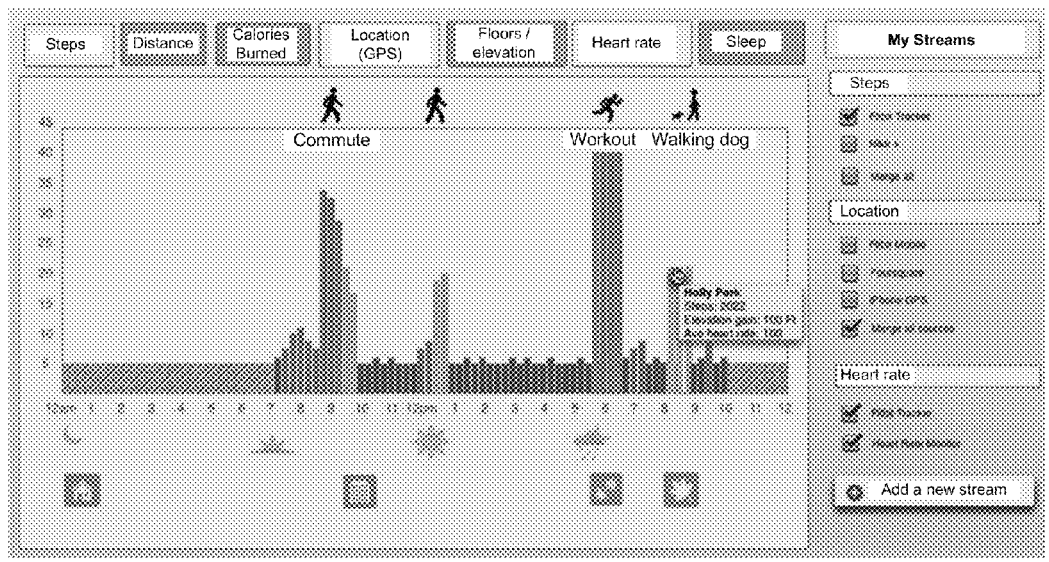

FIGS. 6-8 are diagrams of user interface screens according to several embodiments. In one embodiment, data streams are combined using a hierarchical prioritization structure. A user's account may be loaded with the hierarchical prioritization structure by default. In this context, a user account refers to an online account which provides a repository for user's data. In one embodiment, the user account is managed by a server. A user account may also provide visualization of user data through a website, for example.

In one embodiment, the user is able to modify the user data through such a website as shown in FIG. 6. Each data class collected by each device may be given priority, either above or below any other device's corresponding data class. For example, if a user has a biometric monitoring device clipped to their waistband and another biometric monitoring device located in their shoe, where both measure steps taken, the data class "Step Count" may give a higher priority to the device located in the shoe if the device is more accurate at counting steps. If both devices also measure altitude gained, data from the monitoring device on the waistband may be given priority if the device is more accurate for the "Altitude Gained" class of data. In this case, the shoe's pedometer "Step Count" data class has priority over the waistband pedometer. However, the shoe's pedometer "Altitude Gained" data class has a lower priority than the waistband pedometer. This illustrates that a single device may have different priority assignments for different data classes. This method may be extended to a plurality of devices and data classes.

In another embodiment, a user wears multiple devices in multiple locations in or about the body. In some cases, more than one device is worn in the same location. Examples of locations where devices are worn or carried include, but are not limited to: on a hat, a headband, an earring, a necklace, an upper arm band, a lower arm band, a wristband, a belt, a ring, around the chest (as in a chest band), the waist band, a pocket (shirt, coin, pants, jacket, etc.), shirt collar, ankle, shoe, etc. For example, a user may wear a device on their wrist (e.g., in a watch or bracelet) and a device on their waistband. In this case, the wrist-mounted device data is prioritized over the data of the waistband for swimming stroke rate if the wrist-mounted device is more accurate for that specific data type. In another example, the waistband-mounted device step data is prioritized over the wrist-mounted device step data.

The default prioritization hierarchy may be determined solely by the accuracy of the streams. In another embodiment, one or more additional data stream characteristics may be used to determine the default prioritization hierarchy including but not limited to precision, measurement frequency, and syncing frequency. In some cases, users are able to modify the default prioritization hierarchy. Data regarding users' changes to the default prioritization hierarchy may be used to modify the default prioritization hierarchy for new users.

In an embodiment, the user has the ability to change the default prioritization hierarchy, as shown in FIG. 6. This action can be performed through one or multiple monitoring devices, through client software on a computing device, or through a web browser or Internet application on a computing device. The user can choose 602 to change data stream prioritization 604 permanently, temporarily, or on an event basis (e.g., a single walking exercise). In the case that the change in priority is temporary, the user can choose the duration that the change is active.

In the embodiment shown, the user interface graphically displays (in a line graph in this example) the different data streams the user can choose from. In an embodiment, the user interface is part of a web page. Alternatively, the user interface is a feature of software, or an application on a computing device such as a laptop, desktop computer, or mobile computing device such as a smartphone or tablet.

In the embodiment of FIG. 7, the user may prioritize the different data streams 702 by using a drag-and-drop interface. In order to change the priority of the data stream, the user clicks on the selected data stream, and while holding the click, the user moves the data stream up or down within the list of data streams.

In another embodiment, data stream prioritization is provided automatically through heuristic rules, also referred to herein simply as "rules." For instance, the maximum, minimum, or mean of two conflicting pieces of data are taken as an estimate. The heuristic rules are subject to various criteria such as, for instance, a quality metric derived from the devices. For example, a quality metric for location data originating from a GPS device can be derived from the number of satellites acquired. In the case of Wi-Fi and cell tower location determination, the number of Wi-Fi routers and cell phone towers, the certainty of their position, and their proximity to the user may determine the quality metric.

In some cases devices have a measurable, known quality metric that is considered static or unchanging. For example a Dual X-Ray Absorptiometry (DEXA) body fat measurement device may have a well-defined margin of error in its measurements. A user's body fat may also be determined by Bioelectrical Impedance Analysis (BIA) which may also have a well-defined margin of error in its measurements. If there is data from a DEXA scan and a BIA measurement for the same time period, the DEXA data may be prioritized because it has a higher accuracy. The BIA device may be calibrated or adjusted with the data of the DEXA. DEXA is just one example of a body fat measurement method. Hydrostatic weighing is also suitable as a high accuracy body fat measurement method.

A single device may have varying quality metrics based on how the device is used. When a quality metric is used to determine the prioritization of the data stream, the same device may have varying data stream priority based on how the device is used. For example, a blood pressure cuff measurement, when worn on the wrist, may be given a lower quality metric, and/or data stream priority, than a blood pressure cuff measurement on the arm. Similarly, an optical heart rate measurement of the finger may be given a higher quality metric, and/or data stream priority, than a measurement made by the same device on the wrist, as a measurement on the finger is likely to have a higher accuracy. The location where the device is worn may be determined though methods including but not limited to those described in U.S. Pat. No. 8,386,008.

In certain cases, data from one device may overwrite data from the same device acquired at a different period of time if certain conditions are met. In one example, the conditions for overwriting data may require that the overwriting data have a higher quality metric and be within a certain time window of the overwritten data. For example, a user takes a measurement of their blood pressure at 8:45 am wearing the cuff on their wrist, and then takes another measurement of their blood pressure at 9:00 am wearing the cuff on their upper arm. The measurement made at 9:00 am can overwrite the previous measurement if the conditions for overwriting data are that a new measurement must be within 30 minutes of the one being overwritten and that it must have a higher quality metric.

FIG. 8 is a user interface screen showing data from all sources merged and displayed as a graph, according to one embodiment. The data for FIG. 8 is collected over the course of a user's day, as illustrated below with reference to FIG. 9. FIG. 8 shows the level of activity of the user over a 24-hour period. A graph bar shows the level of activity, and for each 15-minute interval the level of activity is represented according to the size of the bar.

Several metrics can be displayed on the screen, and buttons on the top allow the user to select the metric, such as steps, distance, calories burned, location (GPS), floors/elevation, heart rate, and sleep.

Additionally, the charge may be annotated based on known activities of the user, such as commuting, working out, walking the dog, etc. Further, if the user clicks or hovers the mouse pointer over a period of time, an information window presents more details on the activity, such as the location, the actual number of steps during that interval, elevation gain, etc.

On the right side, the user is able to select which streams, from a plurality of possible streams, to display on the bar chart. In one embodiment, multiple values can be represented simultaneously on the graph bar, such as for example using different colors for each of the parameters. The streams may be labeled according to the device that obtained the data and according to the type of data, such as steps, location, or heart rate. Additionally, a button is provided for the user to add new streams of data.

It is noted that the embodiments illustrated in FIG. 8 are exemplary. Other embodiments may utilize different layouts, data charts, data points, option buttons, data streams, etc. The embodiments illustrated in FIG. 8 should therefore not be interpreted to be exclusive or limiting, but rather exemplary or illustrative.

Figure 9:
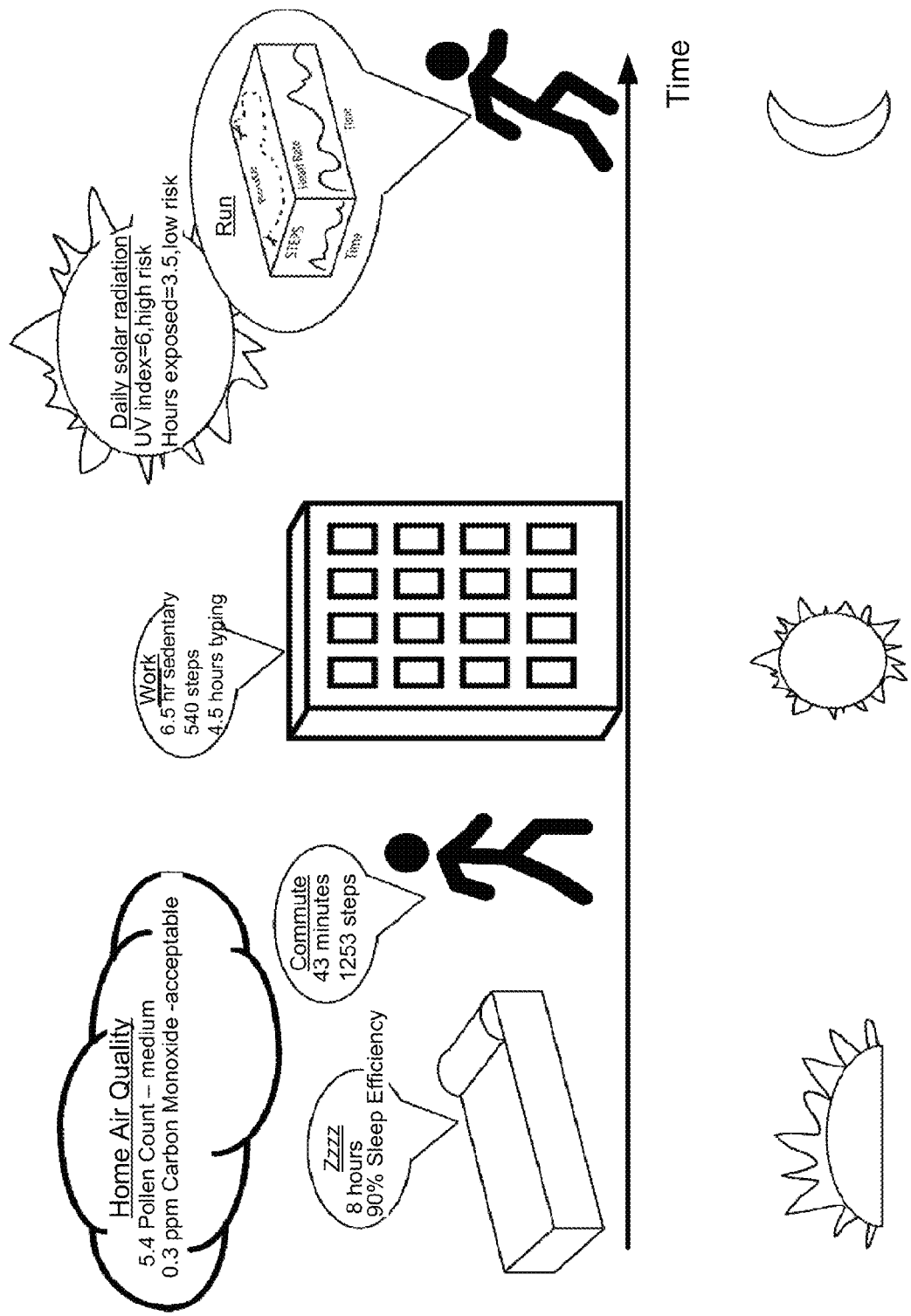
FIG. 9 is a diagram illustrating data that could be collected during a person's daily routine.

FIG. 9 is a diagram illustrating data that could be collected during a person's daily routine. The one or more tracking devices may capture different types of data and identify different states of the user. For example, the system may identify when the user is sleeping, commuting, working, outdoors, running, at the gym, etc.

For each of the states of the user, different biometric and environmental parameters may be captured, such as the pollen in the air, the amount of carbon monoxide in the air, how many hours the user slept, how much time the user spent commuting, how much activity took place during the workday, how much solar radiation exposure, how many steps climbed, etc.

As the user goes about their day, the user may utilize different trackers. Sometimes, the user may have multiple devices tracking user activities, such as a pedometer, a mobile phone, the step tracker, etc.

Embodiments presented herein consolidate the information obtained from multiple devices to provide the best available picture to the user about the user levels of activity, activities associated there with, environmental factors, etc.

However, when the same information is provided by two different trackers, there can be two different data points and the system provides heuristics to determine what is the best data point, or if a combination of the data points is the best approach. For example, if two different devices are tracking the heart rate of the user, in one embodiment, the consolidated data includes the highest peaks and valleys of the heart rate chart.

Sometimes a statistical combinations or measurements are used to consolidated data. For example, the consolidated data may include one or more of average, medium, maximum, or minimum of the multiple data points.

Figure 10:
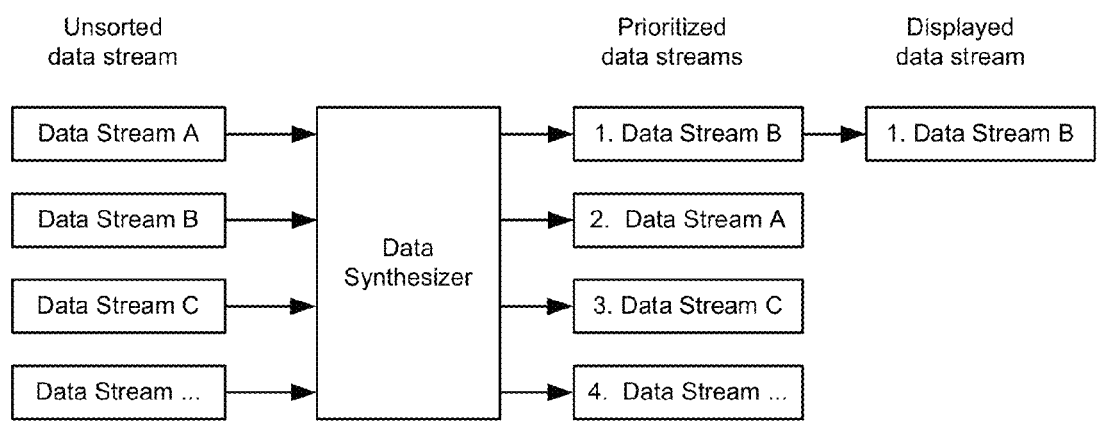
FIG. 10 is a block diagram of data stream synthesis according to one embodiment.

FIG. 10 is a block diagram of data stream synthesis according to one embodiment. In one embodiment, a user prefers to wear a specific device during the day, for example one which is clipped to the belt, and a different device at night which is more comfortable for sleeping, such as a wrist band. The data synthesizer can use the belt clip device data during the day time, when the wrist band shows no activity, and the wrist band device data during the night, when the belt clip shows no activity. In such a case, the two devices may not be given a "priority" over each other. Indeed, the data synthesizer may not have any prioritization structure at all. Instead, in one embodiment, data streams may be selected solely on the activity level.

In some cases, device data stream priority is used in addition to activity level to determine the selected data stream. In one embodiment, a user wears a belt clip device and an anklet device during the day, and a belt clip device and a wrist band device at night. Assuming the anklet data stream is given priority 1, the wrist band priority 2, and the belt clip priority 3, the data synthesizer shows the data from the anklet device during the day because the anklet device data has the highest priority of the active devices for that time period, and the wrist band device at night because the wrist band device has the highest priority of the active devices for that time period. The anklet has a higher priority than the wrist band, but the anklet is not active at night.

A similar scheme is applicable to gaps in data due to syncing delays. For example, a user uses a pedometer and another device that measures the distance a user walks. The pedometer may have synced more recently than the other device. The device that has not synced recently may have a higher priority for the "distance walked" class of data (for example, a GPS device vs. a pedometer). In this case, the pedometer data is used for the time period between the time of the last GPS device sync and the time of the more recent pedometer sync. When the GPS data syncs, the data synthesizer can replace the distance data from the pedometer with that of the GPS.

In one embodiment, the system stores all the sensor data (either locally in the device or remotely in the server), so it is possible to reconcile the data stream for different use cases when new data is available, even going back in time and reconcile historical data with the newly available data. In one embodiment, a storage database keeps all the data collected, as well as the reconciled data, also referred to herein as consolidated data, which is the result of combining two or more data streams. Further, it is possible to do further reconciliation of historical data by going back to a specific time period and request the system to perform a reconciliation of the multiple data streams.

Figure 11A:
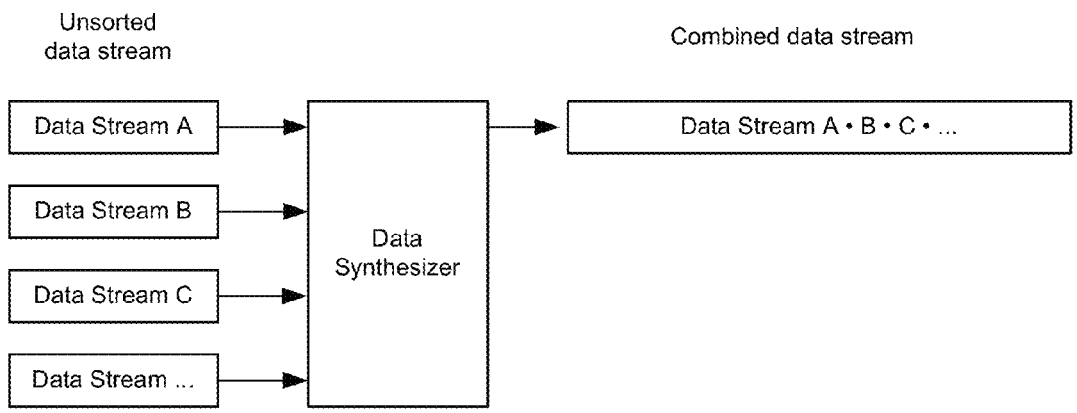
FIG. 11A is a block diagram of data stream synthesis according to one embodiment.

FIG. 11A is a block diagram of data stream synthesis according to one embodiment. In one embodiment, multiple data streams of the same type are combined using one or more methods. One method of combining data streams of the same type is to average them. Other methods include a weighted average where the weight of one data stream over another is proportional to its accuracy. For example, if the two or more data streams have a probabilistic measure of accuracy, then the combined estimate is taken as the expectation. It may also be taken as the most likely (i.e., the value with the highest probability of being correct).

The algorithm that is used to combine data streams changes depending on various factors including the number of data streams, the quality of data streams (precision and accuracy), and the source of the data streams (which model device, first party or third party, etc.). In some embodiments, the algorithm uses rules that define priorities for the data streams and methods of combining the data from the multiple streams to create a consolidated data stream having information from one or more multiple sources.

When one device does not acquire data for a certain period of time, the data synthesizer is able to maintain a continuous data stream by filling in the gap with data from other devices. The data synthesizer can fill in the gap of data even if one device's data has a lower priority than another device that was not acquiring data. In some cases, more than one device may have the same priority. In such cases, the device that is currently measuring data can be used. This is useful in cases when one device is not able to measure data, for example because of low battery.

In one embodiment, the data stream which has data that shows characteristics of being used is selected by the data synthesizer. For example, for the step counts data stream, the data stream which has step counts greater than zero is selected because having more than zero steps is characteristic of the device being used. In another example, an accelerometer data stream shows characteristics of being worn when a certain pattern of accelerations is detected.

Figure 11B:
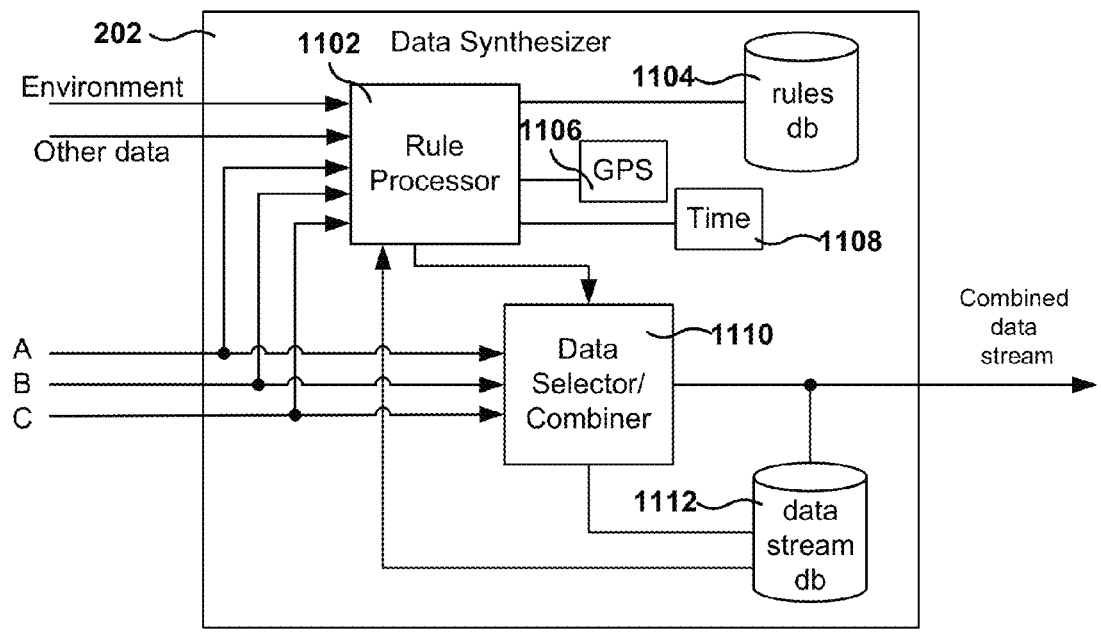
FIG. 11B illustrates an exemplary architecture of the data synthesizer, according to one embodiment.

FIG. 11B illustrates an exemplary architecture of the data synthesizer, according to one embodiment. In one embodiment, the data synthesizer 202 includes rule processor 1102, rules database 1104, the GPS module 1106, a timekeeper module 1108, a data selector/combiner module 1110, and a data stream database 1112.

Data synthesizer 202 receives one or more data streams A, B, C, environmental data, and any other type of external data that may have information regarding user activities (e.g., user calendar). The rule processor identifies the incoming data from the data streams, environmental data, and other data, and analyzes the pertaining rules to apply them to the incoming data. In one embodiment, the rules database 1104 keeps track of the rules, but the rules may be stored elsewhere and might be change over time to fine-tune the performance of the data synthesizer 1102. In one embodiment, the user is able to create rules for prioritizing data, such as identifying the user's favorite (i.e., highest priority) device.

After evaluating the different rules, the data selector/combiner consolidates, also referred to as reconciles, the multiple data streams to create a consolidated data. As used herein, consolidated data refers to the analysis of data received from multiple sources to generate a data source with information available for presentation to the user. For example, consolidated data may include filling gaps in the data stream from one device with data from another device, selecting which data to choose when multiple sources of data provide information about the same event (e.g., step counts during a certain time interval), or any combination thereof.

For example, a user may have three different data streams from three different trackers. One of them may indicate that the user is at work, while the other two indicate that the user is at home. However, the rule processor 1102 checks the user's calendar, and the calendar indicates that the user is at work, so the data selector 1110 may use the data from the tracker that is in accordance with the calendar, even though that tracker may be in the "minority." Therefore, external data may be used to determine the priority of different data sources. Also, external data may be used to determine priority with data that is not in the data stream.

In another example, the data synthesizer has access to calendar and contact information for the user. The contacts may have addresses identifying a location, and based on the physical location of the contact, the data synthesizer may derive that the user is at the country club, so walking activity may be associated with the activity of playing golf. In this case, the data from a tracker may be given higher priority when considering that the user is playing golf.

Any method for capturing data may be used for the embodiments. For example, data may be acquired via and API to access a web service (e.g., a web service that captures data for one of the trackers of the user). If the user provides login information for the external website, data synthesizer 202 may access the web service using an API or some other data exchange mechanism.

In one embodiment, the data is reconciled as the data comes in, that is the data is reconciled "on-the-fly," and the combined, or consolidated, data stream is provided as an output stored in data stream database 1112. In some embodiments, the data is reconciled during predetermined time periods (e.g., at night once a day). Sometimes there are delays when capturing the data, so the actual reconciliation with all the available data is done when all the data, or at least data from a plurality of devices, is available. In some embodiments, the same data may be reconciled multiple times; as more data becomes available, new reconciliations may overwrite previous reconciliations.

In one embodiment, data stream database 1112 is a time series database. A time series database server (TSDS) is a software system that is optimized for handling time series data, such as arrays of numbers indexed by time (e.g., a date-time or a date-time range). Sometimes the time series are called profiles, curves, or traces. TSDS are often natively implemented using specialized database algorithms. However, it is possible to store time series as binary large objects (BLOBs) in a relational database or by using a VLDB approach coupled with a pure star schema. Efficiency is often improved if time is treated as a discrete quantity rather than as a continuous mathematical dimension. Database joins across multiple time series data sets is only practical when the time tag associated with each data entry spans the same set of discrete times for all data sets across which the join is performed. The TSDS allows users to create, enumerate, update and destroy various time series and organize them in some fashion. These series may be organized hierarchically and optionally have companion metadata available with them. The server often supports a number of basic calculations that work on a series as a whole, such as multiplying, adding, or otherwise combining various time series into a new time series. The server can also filter on arbitrary patterns defined by the day of the week, low value filters, high value filters, or even have the values of one series filter another. Some TSDSs also provide statistical functions for synthesizing multiple sources of data.

In one embodiment, the data streams are saved in the time series database as the data comes in. In addition, summary series are precalculated in some embodiments; for example, summaries can be calculated for reconciled data for one hour, two hours, daily, weekly, etc.

The use of a time series database facilitates the easy extraction of data from the database to present many types of graphs or many types of data made available to the user. For example, a user wants a count of all the steps taken in a year. In one embodiment, the step count is stored as minute data, meaning that the number of steps taken in one minute is stored in the database together with the timestamp. In this case, the user has data for three different trackers that have been used throughout the year. If the system calculates the summary for each of the data streams separately, the final step count may be different for each of the devices, among other reasons, because some devices may not be in use while other devices are in use. In order to get the reconciled total, a reconciliation is made for these three data streams to obtain a resulting data serious that accounts for the step counts throughout each interval (e.g., a minute). In other words, the reconciliation calculates the step count for each minute of the year by looking at the data provided for that minute by all three devices. Once the reconciliation is made by minute, the total for the year is calculated and presented to the user.

As the data comes in, the data synthesizer 202 makes the determination of whether to store all the incoming data, or reconcile the incoming data, or both.

It is noted that the embodiments illustrated in FIG. 11B are exemplary. Other embodiments may utilize different modules or group the modules into other configurations, as long as the described functionality is provided by data synthesizer 202. The embodiments illustrated in FIG. 11B should therefore not be interpreted to be exclusive or limiting, but rather exemplary or illustrative.

Figure 11C:
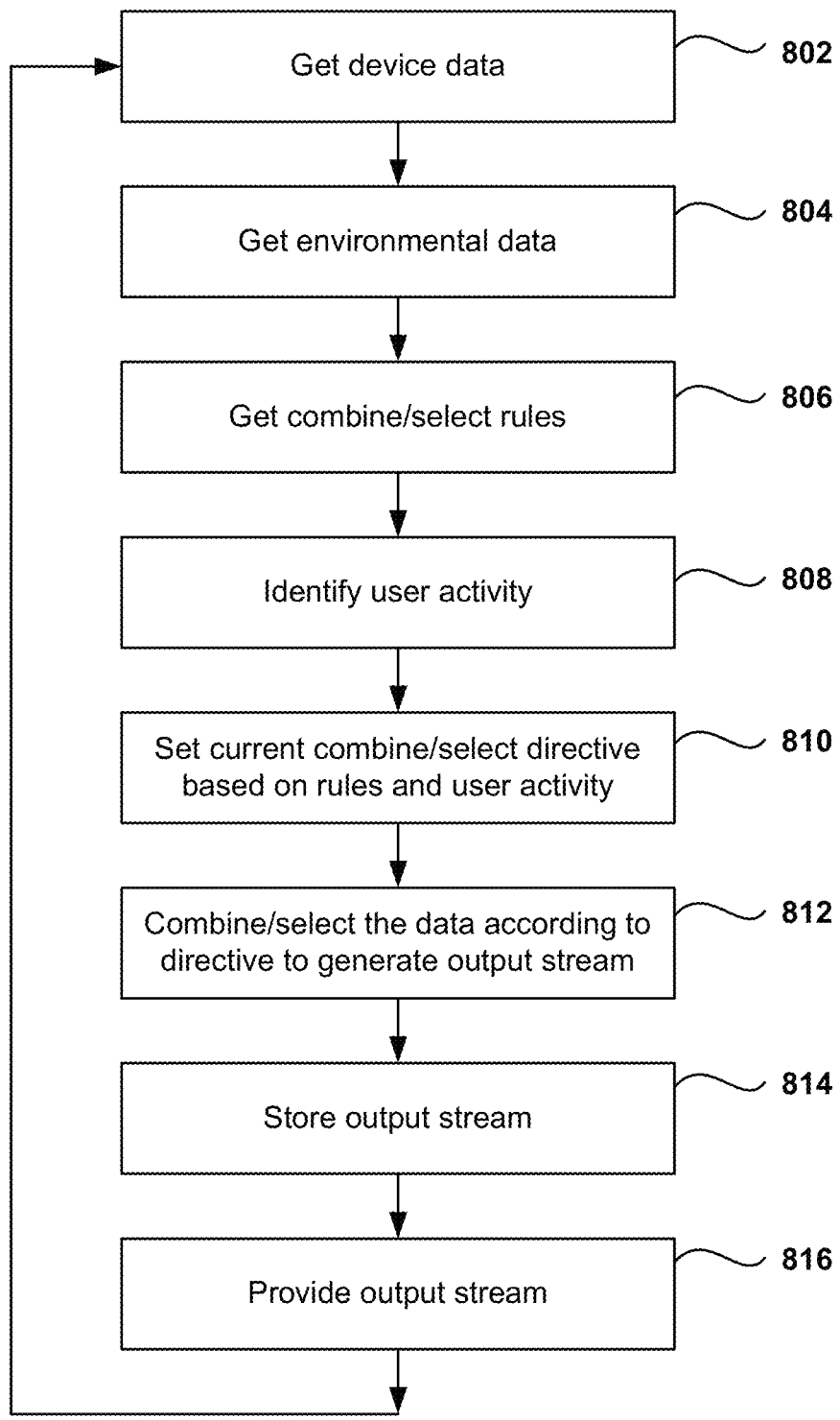
FIG. 11C is a flowchart of a method for combining multiple data streams, according to one embodiment.

FIG. 11C is a flowchart of a method for combining multiple data streams, according to one embodiment. In operation 802, device data is obtained from one or more tracking devices. From operation 802, the method flows to operation 804 where additional data is obtained, such as environmental data (time, temperature, whether, barometric pressure, etc.). However, in one embodiment, operation 804 is optional and the data reconciliation only applies to data streams from tracking devices.

From operation 804, the method flows to operation 806 where the rules for combining or selecting data are obtained. In one embodiment, the rules are kept in rules database 1104 of FIG. 11B, but in other embodiments, the rules database may be stored in other places, such as in the server memory.

From operation 806, the method flows to operation 808 where the user activity is identified for one or more time periods, based on the obtained data and the obtained rules. From operation 808, the method flows to operation 810 where the system sets a directive for combining or selecting data based on the rules and user activity. This directive is used to identify the process by which data is to be combined from the multiple data streams.

From operation 810, the method flows to operation 812 where the data from the multiple data sources is combined or reconciled based on the directive identified in operation 810. The result is an output data stream of consolidated data, also referred to as reconciled data.

The output stream is stored in operation 814. In one embodiment, the output stream is stored in data stream database 1112 of FIG. 11B. In operation 816 the output stream is provided to the user or to another computing device (e.g., a smart phone).

While the various operations in this flowchart are presented and described sequentially, one of ordinary skill will appreciate that some or all of the operations may be executed in a different order, be combined or omitted, or be executed in parallel.

Figures 11D, 11E:
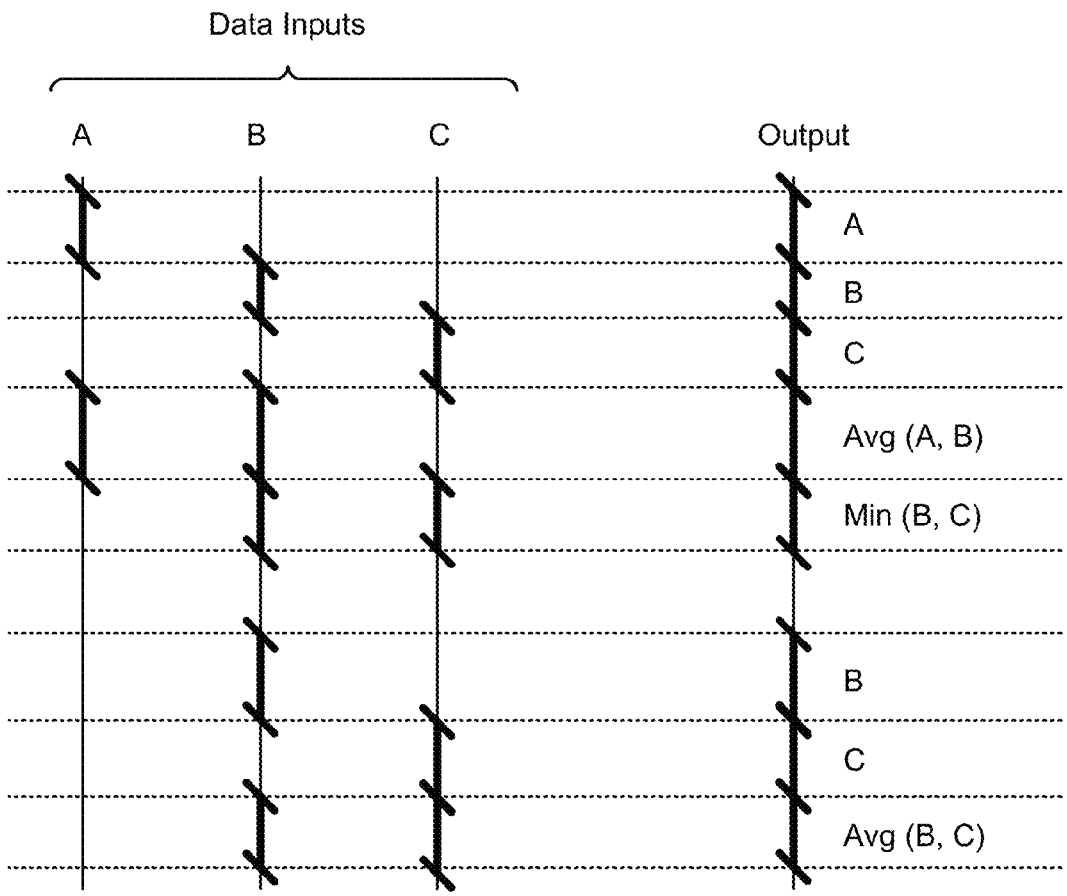
FIG. 11D is an exemplary rules database according to one embodiment.
FIG. 11E illustrates the selection of different inputs, based on combination rules, to generate a compound output, according to one embodiment.

FIG. 11D is an exemplary rules database according to one embodiment. The rules database includes one or more rules that identify a trigger (which can be a combination of one or more conditions) and an action (which can be a combination of one or more actions). For example, a first rule selects Device A when the user is running, a second rule selects Device B when the user is sleeping, a third rule calculate the average of the data provided by devices A in C when the user is detected to be climbing steps, etc.

Consider a user wearing a step tracker and a swim tracker. If the data from the swim tracker is present for a given interval with data from the step tracker during the same interval, then the data of the step tracker can be removed (or at least not presented to the user) in favor of the swim data.

Consider a user using an activity tracker and a treadmill concurrently. The data synthesizer uses the following rules in an embodiment to determine which data to select:

1. Treadmill distance overwrites tracker distance.
2. Tracker steps overwrites treadmill steps (if any).
3. Treadmill overwrites tracker stair gain (using slope information, or just to 0 if the tracker counted any floors).
4. Treadmill calories overwrites tracker calories.
5. Treadmill distance measurement is used in the auto calibration of tracker stride length and/or calorie burn rate.

Similar structures are used for different exercise equipment, including but not limited to elliptical trainers, stair masters, stationary bikes, rowing machines, weight machines, etc.

In another embodiment, a swim tracker takes precedence over a step tracker, and overwrites calories, floor count, etc., (whether wrist, head, or body mounted). In another embodiment, a sleep tracker overwrites steps (when the user is considered asleep), calories, and floor count, from other devices. Other monitoring devices that are incorporated into similar data stream prioritization structures include, but are not limited to, free weight trackers (devices attached to free weights or mounted on arms/body), sitting trackers (devices mounted in seat), sleep trackers (pillows/beds, motion/heart rate), alarm clocks (sound), head-mounted EEGs, and shoe trackers (inside the shoe or attached to the shoe for tracking distance/speed, sometimes including a GPS unit).

The algorithms for rule selection, operation, and modification may be self-learning or self-tuning in various embodiments. For instance, the user may wear a device for calorie burn that is considered the "gold standard" (i.e., preferred) device (because of its accuracy, for example) over other devices. The system of devices or the individual devices can develop a neural network (or other learning algorithm, or merely adjust algorithmic parameters) to train the devices to match the output of the gold standard device.

What is considered the gold standard (i.e., with the highest priority) may change with the context of use. For example, data can be received from an elliptical machine and from a body-worn motion-based activity tracker. The body-worn activity tracker, in an embodiment, learns to (a) identify the motion signature that indicates use of an elliptical machine in order to automatically detect when the user is using an elliptical machine, and (b) use algorithms tuned for, or adapted to, the elliptical machine.

In another embodiment, the body-worn tracker has physiological sensors (e.g., heart rate, blood glucose, etc.) that are used for similar purposes. In another embodiment, the use of a location aware portable device such as a GPS-enabled phone or tracker may detect that the user is driving, or is in a private or public vehicle such as a car, train, or bus. This information is used to correct erroneous step counts on a step-counting device and/or to train the step-counting device to recognize the motion signature of the vehicle. In one embodiment, this motion signature is detected by sensing vibrational patterns with a motion sensor such as an accelerometer.

In various embodiments, the data synthesizer uses machine learning tools including, but not limited to neural nets, k-means, nearest neighbor, support vector machine, naive Bayes, Bayesian network, expectation-maximization, and decision trees.

FIG. 11E illustrates the selection of different inputs, based on combination rules, to generate a compound output, according to one embodiment. Three data sources A, B, and C, provided data streams that are being consolidated into a single output. In the first period, only data from Device A is available, therefore, the output is the data from Device A. Similarly, in the second period, only data from Device B is available so the output corresponds to the data from Device B.

In other periods, data may be available from two or more devices, and the consolidated data may correspond to the data from one of the devices, or to a combination of the data from the multiple devices. For example, in the fourth period, the output is the average of the data from devices A and B, and in the fifth period the output is the minimum of the data from devices B and C.

In one embodiment, a voting system is used to define the output. In a voting system, the output is selected by identifying data points that are grouped in clusters, or in other words data points associated with the value that corresponds to the approximate value provided by a majority of devices. For example, during a time period the following step counts, taken by multiple devices, are available: 22, 23, 20, and 100.

The average value of these step counts would be 41.25, which isn't consistent with any of the data taken by any of the devices. Therefore, the average would not be an accurate measurement of the step count. Using a voting system, the system identifies that the majority of values are grouped around a cluster of around 22 steps. The value of 100 is discarded as being outside the cluster, and then the average of the values in the cluster (21.6), or the median (22), is selected as the data point for the output. The voting system provides an algorithm for filtering noise by discarding values that appeared to be anomalous.

In some embodiments, devices may learn to infer phenomena that the devices cannot directly measure. For instance, if the user wears a heart rate monitor and a motion-based activity tracker, a correlation model can be made to infer a user's heart rate even when the user is not wearing the heart rate monitor (but the user is wearing the motion-based activity tracker). In another example, if a user wears a heart rate monitor and a location aware device, such as a GPS, a correlation model infers the user's speed even when the user is not wearing the location aware device. In another example, the distance measured by a location aware device such as a GPS is used in combination with the number of steps measured by a pedometer to create an accurate measurement of the user's stride length. This measurement is subsequently shared with the GPS device and the pedometer so that the GPS device can estimate the user's steps taken, and so that the pedometer can estimate the distance the user has traveled independently of the other device. In the case that the GPS and the pedometer are integrated into the same device, the GPS can use the pedometer to create an estimate of the distance that the user has traveled since the last satellite acquisition to aid in determining the user's location.

In another embodiment, a plurality of devices is used to infer data that no single device can accurately measure or infer. For example, if a user uses a heart rate monitor, a blood pressure monitor, and a bioelectrical impedance analysis (BIA) device, the data synthesizer can infer the user's blood pressure using a BIA measurement and a heart rate measurement.

Figure 12:
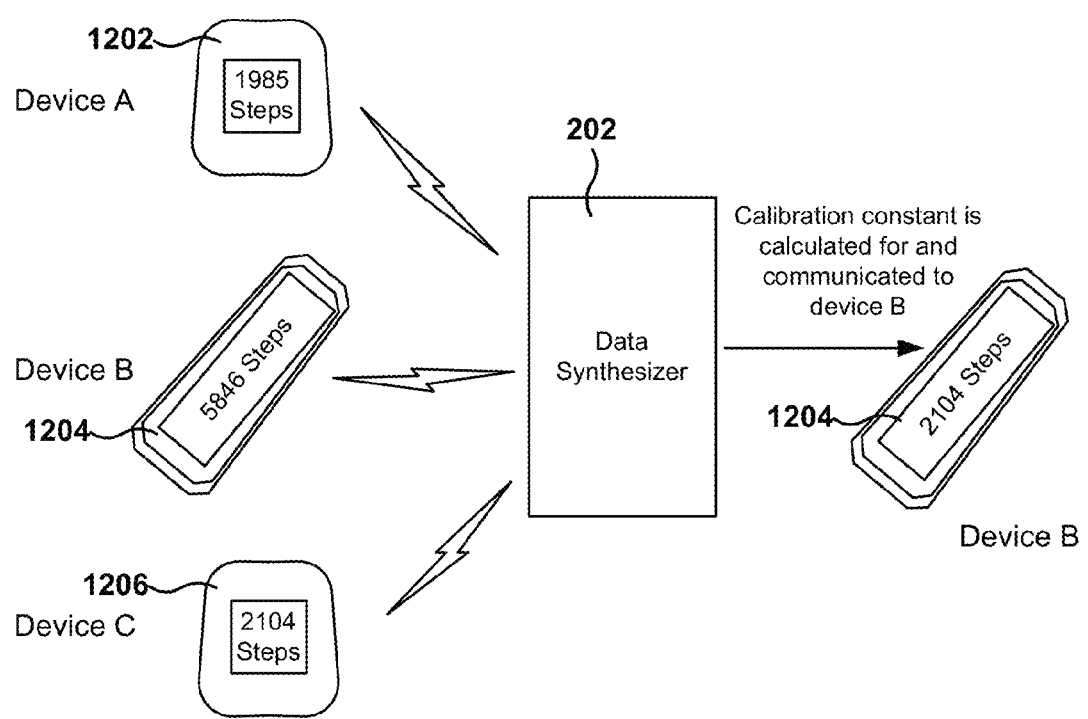
FIG. 12 is a diagram of data stream synthesis from multiple devices according to one embodiment.

FIG. 12 is a diagram of data stream synthesis from multiple devices according to one embodiment. However, it should be noted that the data synthesizer can also use data streams from multiple users to improve the data quality of a single user.

In one embodiment, the data synthesizer uses the data streams of more than one user to create statistics which are used to set defaults to a single user's account. For example, if a user does not enter their stride length data on their device or on the account associated with the data synthesizer, a default stride length is set for them based on typical stride lengths for users of similar age, height, and gender. Users can opt in or opt out of allowing the data synthesizer to use their data on other users' accounts. Users can also opt in or opt out of allowing other users' data to modify their data.

In another embodiment, the data synthesizer uses a subset of all of the users determined to be more relevant to the individual user. For example, the data synthesizer uses only data from users who have linked accounts through online social connections. Such "shared" data may be used in the method described above to determine a user's stride length if it is not entered by the user.

Other uses of shared data may involve an algorithm which determines when two users have performed the same activity together. For example, if two users have location aware devices that also contain activity monitors, the data synthesizer determines that the two users have completed a workout together, if the users were in a pre-defined proximity at the same time they each had a similar activity level. Once the data synthesizer determines that two users have completed a workout together, the data synthesizer uses the data of the respective users to improve or add to the biometric data collected by each user. For example, if two users go for a walk together, and user 1 had a device with an altimeter and user 2 did not, the data synthesizer can add the altimeter data stream from the account of user 1 for the duration of the walk to the account of user 2. The data synthesizer can also prompt both users to connect socially online by "friending" each other, if the users have not already. Further, the detection of a jointly performed workout or social gathering may be awarded by the data synthesizer as in a virtual badge or activity points.

In another embodiment, the accuracy or trustworthiness of individual sensors (or sensor models or types) is calculated by one or more of a user rating and prioritization settings in the system. The data synthesizer may automatically rank the accuracy of connected sensors (e.g., a particular model of pedometer) based on the information from the data synthesis system. This ranked data may be shared with the user to recommend a more accurate or trustworthy sensor instead of the current sensor. This data can also be used to train the default prioritization settings of new users.

The data synthesizer may export data in various ways. Data streams can be viewed on a web site using any computing device with a web browser or appropriate mobile application (app). A user can choose to export their data streams to other devices or services. For example, a user may want to have the synthesized data shown on one or more of their biometric monitoring devices. The user may choose to have their data shared with various health monitoring services such as Microsoft Health Vault1M or MyFitnessPal™. The use of a standard data identification and structure aids in the compatibility of third party services, and so enhances the user experience.

In an embodiment, the data synthesizer is able to determine which data streams are the most accurate. With this knowledge, devices that have incorrect data, or have data whose accuracy is lower than the most accurate data, have their data replaced with "better," more accurate data. For example, suppose a user has a pedometer device that uses inertial sensors to determine the distance a user has walked, and also has a GPS enabled device. The data synthesizer can determine that the distance data as measured by the GPS enabled device is more accurate than that of the inertial sensor pedometer. The data synthesizer can update the inertial pedometer with the more accurate GPS pedometer data.

In one embodiment, the determination of which data stream is most accurate is based on predetermined accuracies for specific sensors. In another embodiment, algorithms determine the accuracy of a data stream solely based on the data stream's data and/or the data stream compared to a second data stream which may indicate the accuracy of the first data stream. This can be extended to the comparison of more than two data streams. For example, data from a GPS, inertial sensor pedometer, and location as determined by cellular tower triangulation may be compared to determine which is most accurate.

The data stream synthesizer can also create a function that relates a device's raw data to a more accurate data stream or combination of data streams. The data stream synthesizer compares a single device's data stream to a data stream that is more accurate. The data stream with higher accuracy may be from a device that is known to have higher accuracy, a device that is determined to have higher accuracy through a comparison with other data streams, or it may be from a combination of multiple data streams that together have a higher accuracy than any single data stream. The data stream synthesizer determines a functional relationship between a single device's data stream and the higher accuracy data stream. This functional relationship is shared with the device so that the device can correct its algorithms and improve its accuracy. In one embodiment, this functional relationship is characterized as a calibration. In a case in which the device displays data, this allows the user to see higher accuracy biometric or environmental signals before these signals are uploaded and combined in the data synthesizer.

In one embodiment, the data synthesizer automatically calibrates a user's stride length, or the function mapping of the user's stride length (in the case that the stride length is a function of step frequency, foot contact time, surface slope, etc.). In an embodiment, this is accomplished by using the data stream of a GPS or other location aware device to create an accurate measurement of the distance that the user walks, runs, jogs, etc., in addition to a data stream from a pedometer. The distance as measured from the GPS may also be used in combination with the number of steps measured by a pedometer to create an accurate measurement of the user's stride length.

In another embodiment, the system performs a discrete calibration event. In an embodiment, this involves the user uploading, sharing, or entering high accuracy data with the data synthesizer. This data is then used to calibrate any devices connected to the user's account. For example, a user uploads, enters, or authorizes the sharing of data that was collected from a doctor's appointment using high accuracy equipment including but not limited to data regarding blood pressure, body fat, resting heart rate, height and body weight. Such data may also be used to retroactively correct a user's historical data.

The data synthesizer provides the synthesized data to a user interface so that the user can review data. In an embodiment, the user interface allows the user to perform such tasks as correcting incorrect data, entering biometric data, modifying data stream prioritization settings, entering quality metric data for data streams, setting goals, entering data that is not tracked by the user's devices and interacting socially and competitively with other users. The user interface can also allow the user to quickly review and comprehend data from many different devices with varying sampling frequencies.

The data streams or algorithmic combinations of data streams may be used by the data synthesizer or a computing device connected to the data synthesizer (such as a server) to provide a rich interaction between the user and their data, and between the user and the data of others. In one embodiment the user is presented with a simplified view of all of their data streams. For example, a user's account website shows the user the total number of steps the user has as determined by a combination of all of their step counting data streams in a specific period of time including but not limited to hour, day, week, month, year, and the time period that the user has had an account. Other totals of data are selectively provided to the user in a similar manner including, but not limited to calories burned, distance of walks and/or runs, floors climbed, hours asleep, hours in bed, hours of a specific activity or combination of activities such as walking, biking, running, and/or swimming.

The user is able to compare user's data with the data of other users, and compete with other users or with themselves. For example, the user can choose to be ranked according to one or more data streams in a leaderboard with other users that the users have "friended." The user is able to compare their current data statistics with their own statistics from a different time period. For example, a user is shown how many more or less steps the user took the previous week compared to the current week. A user's data can also be used in virtual contests with set goals, goals based on the user's own statistics, or goals based on other user's statistics. Real or virtual prizes are awarded for winning such a contest. For example, a group of users competing in a corporate wellness challenge win prizes based on data acquired and combined by the data synthesizer.

In an embodiment, a user is awarded a virtual badge for reaching a certain data metric using the data acquired and/or combined by the data synthesizer. For example, a user is awarded a badge for climbing 50 floors in one day. In another example, a user is awarded a badge for taking a total of 10,000 steps since the user started acquiring step data.

Figure 13:
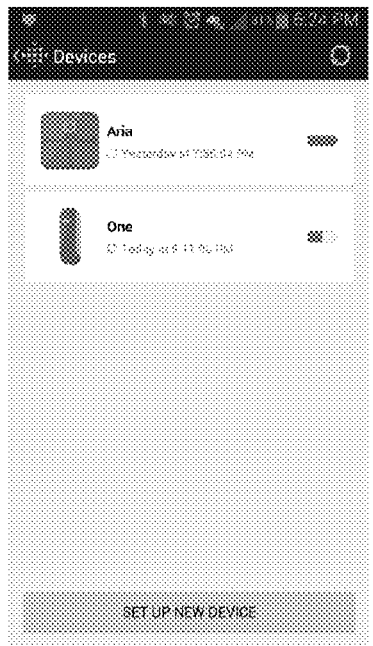
FIGS. 13, 15, and 16 illustrate user interface screens for device management according to several embodiments.

FIG. 13 illustrates an interface on a portable device for configuring tracking devices in use by the user. In one embodiment, a website or application connected to the data synthesizer enables the user to manage the devices that communicate with the data synthesizer. Such a management tool is called a "Device Locker" in one embodiment. In the device locker, the user is able to see all the devices connected to his account, as well as a variety of their characteristics, settings or data including but not limited to battery level, model, name, and last time synced.

The device locker can provide notification of when a device's battery is, or is going to be, critically low. For example, the device locker notifies the user with a pop up dialog stating that the device will only be able to track steps for two more hours before the battery runs out of charge.

In the example of FIG. 13, the user has configured a digital scale and a wearable fitness tracker. If the user selects a device (e.g., touches the area associated with one device), further information regarding the device and its configuration is provided. A button at the bottom of the interface provides an option for setting up new devices.

Figure 14:
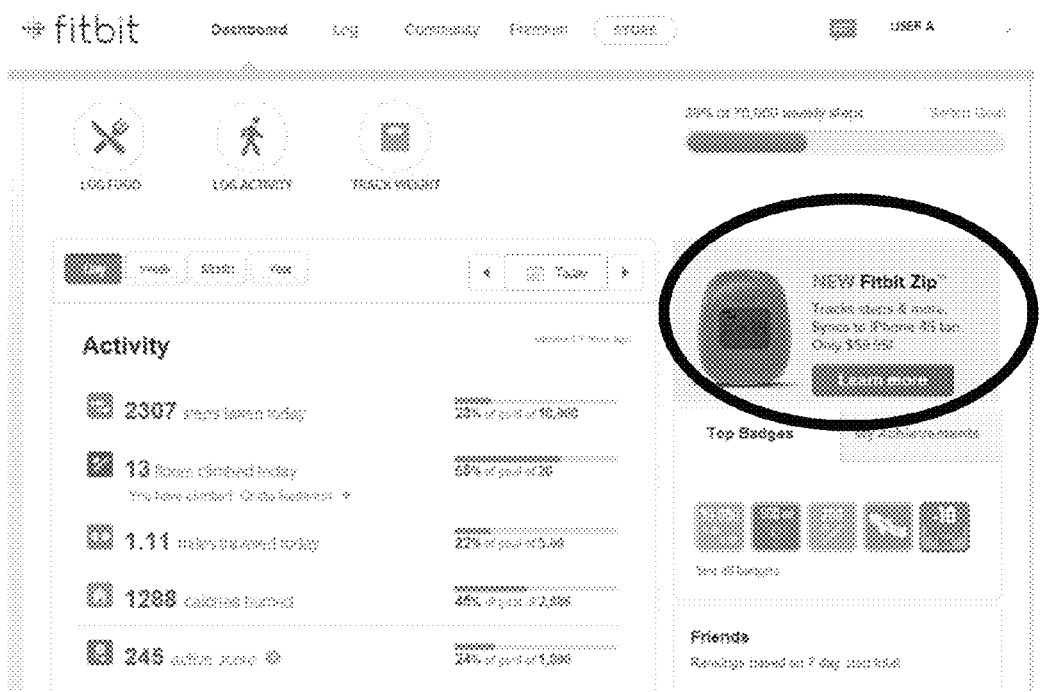
FIG. 14 is a user interface screen with a targeted advertisement according to one embodiment.

FIG. 14 is a user interface screen with a targeted advertisement according to one embodiment. In another embodiment, as illustrated in FIG. 14, it is determined that the user's device lacks some capability or feature that is available on another device. The other device is offered for sale to the user in the form of a link to more information, including purchase information.

Figure 15:
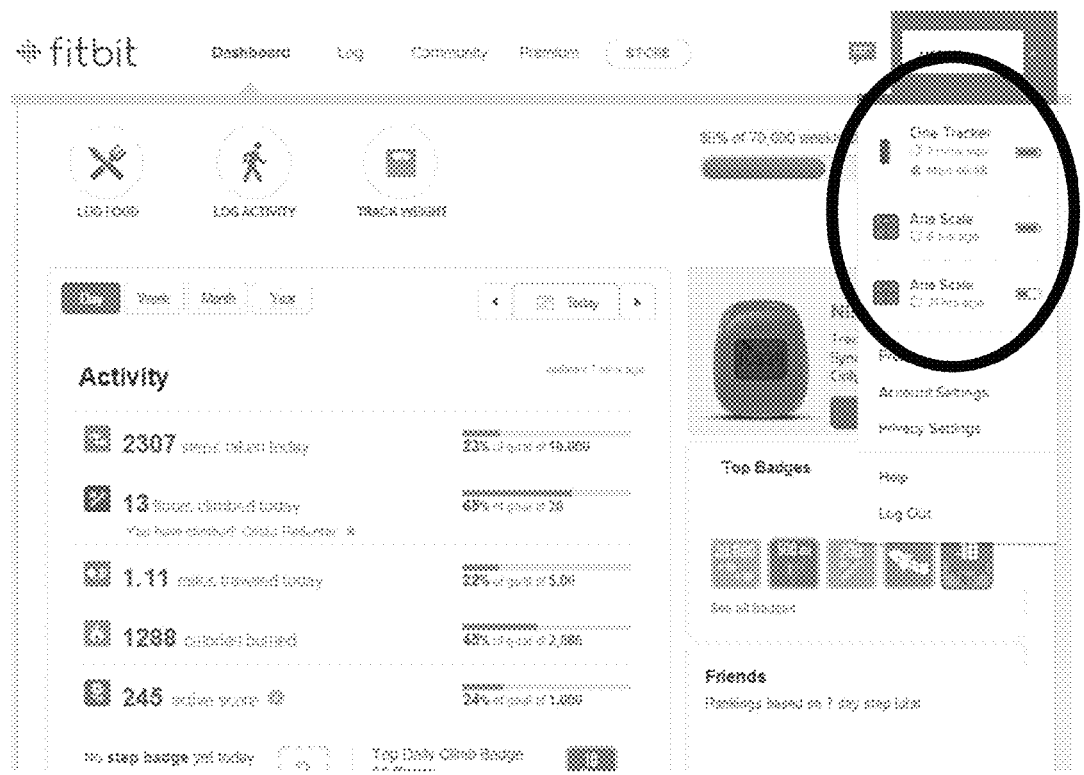

FIG. 15 illustrates an interface that provides information about user activities and tracking devices. The interface includes an area with the active devices, and in the embodiment of FIG. 15 there are three active trackers, a wearable tracker and two different digital scales. For each device, the interface provides information regarding the last time that the device was synced (e.g., 7 minutes ago, 6 hours ago, 21 hours ago) and how much battery is left on the device.

In the embodiment of FIG. 15, the battery level is indicated via an icon that symbolizes a battery with a dark bar inside. The bar indicates how much power is left. A full battery would have a bar completely full (e.g., completely dark), and a empty battery would have an empty bar. In other embodiments, the amount of battery left may be indicated in other ways, such as via a number of the percentage of battery left, or a number indicating the amount of time left before the device runs out of power.

Figure 16:
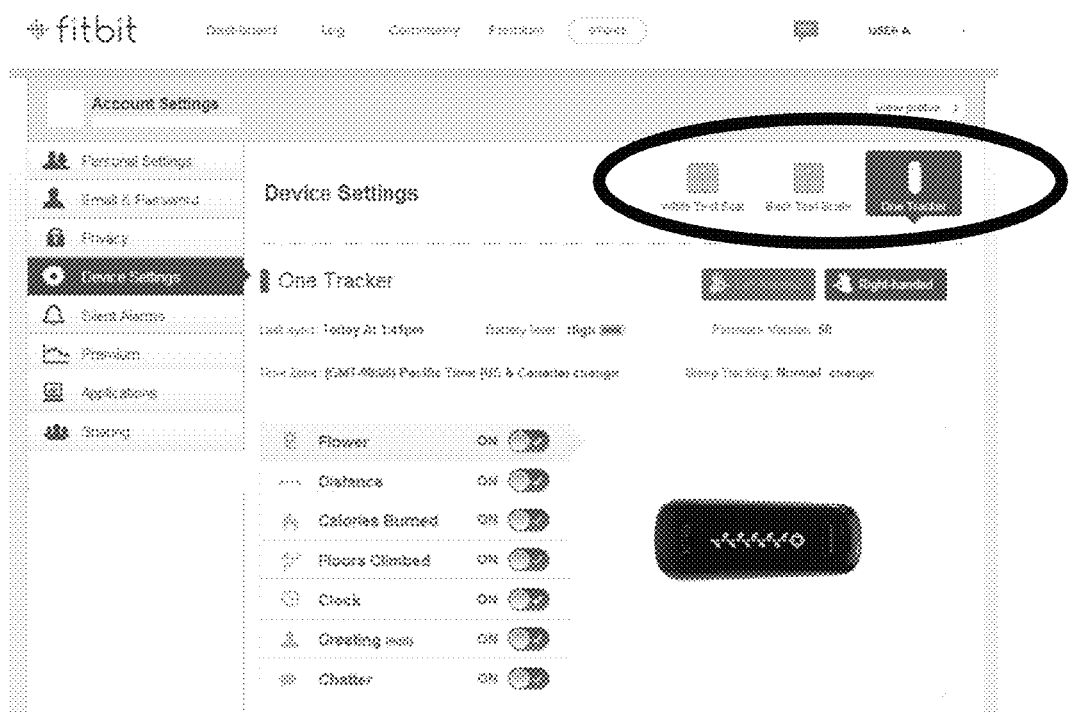

FIG. 16 illustrates an interface for managing a device on the web service, according to one embodiment. When the user selects one of the active tracking device (e.g., clicks or touches on the corresponding device in FIG. 15), the interface of FIG. 16 is presented with information about the selected device. In one embodiment, a list of devices is provided on the page and the user can select one device at a time to view the profile information for the corresponding device.

For example, the device settings for the device may include information about tracking steps, tracking distance, tracking calories burned, tracking floors climbed, setting the clock on the device, changing the greeting on the device, etc. In addition, other options include setting the device for left hand or right hand use, changing the firmware version, information about the battery level, the last time the device was synced, etc.

Figure 17:
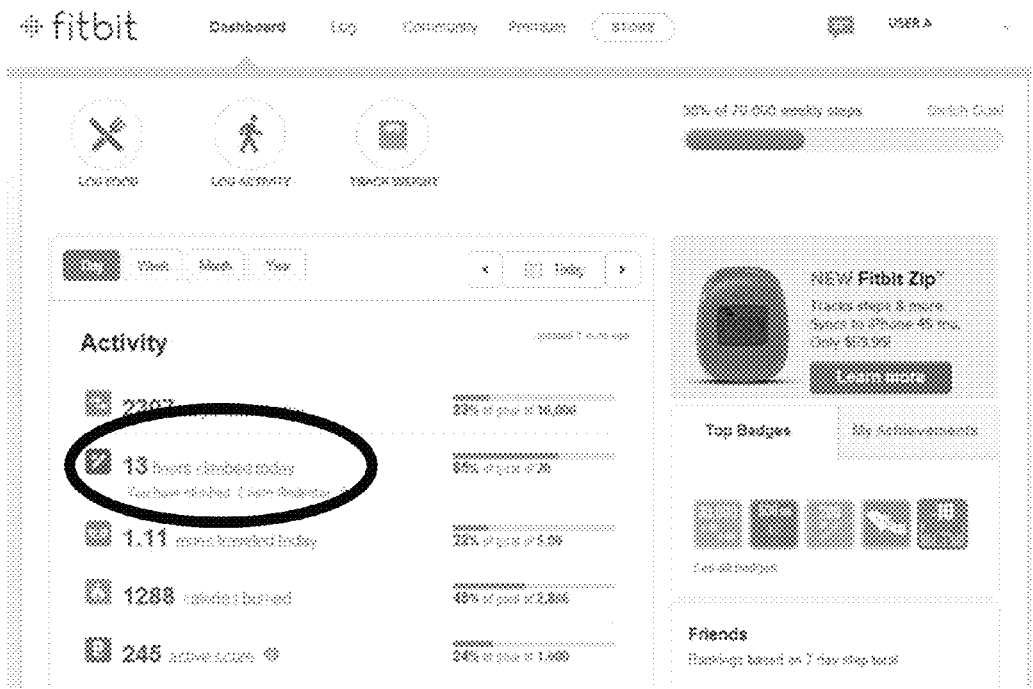
FIG. 17 is a diagram of a user account website page example in which a device is used for measuring or estimating the number of floors climbed, according to one embodiment.
Figure 18:
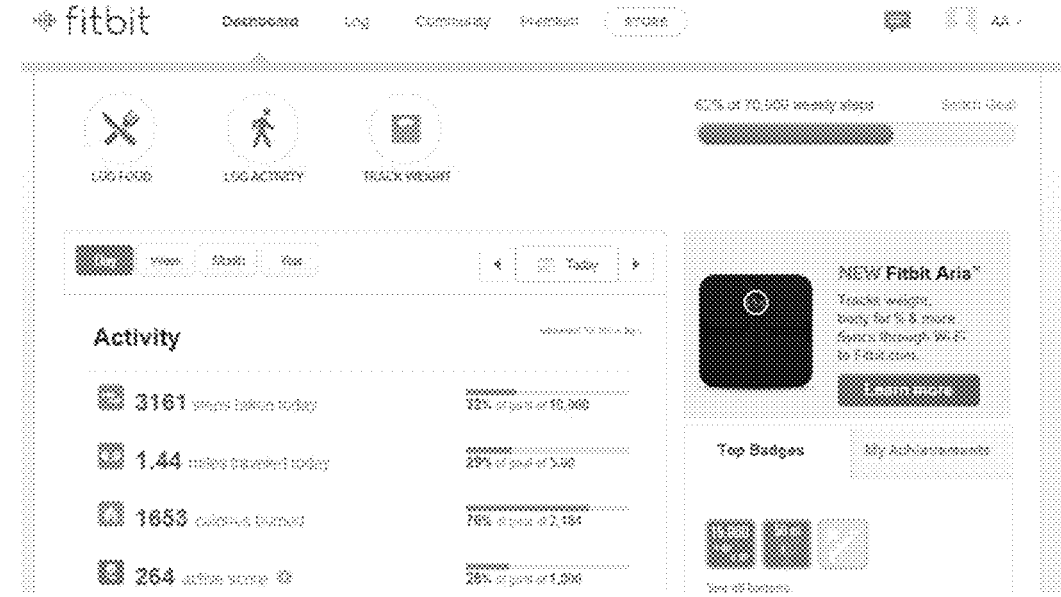
FIG. 18 is a diagram of a website page for a device which cannot track the number of floors climbed, according to one embodiment.

FIG. 17 is a diagram of a user account website page example in which Device A has the ability to measure or estimate the number of floors that a user has climbed. Metadata of a data stream or data streams, or characteristics of devices linked to a user's account are used in embodiments to improve the presentation of data to the user. For example, if a user has a device or devices that track steps and distance walked, the user's account website is configurable to show only those two metrics. In another example, if the user's devices can collect data about the user's sleep, but the user never or infrequently uses this device feature, the user's account omits any metrics regarding sleep. FIG. 17 is a diagram of a user account website that shows an example in which Device A has the ability to measure or estimate the number of floors that a user has climbed. FIG. 18 shows the same data presentation website for a different device which cannot track the number of floors climbed. In this case, the number of floors climbed is omitted from the data presented.

In another example, FIG. 17 shows the website for a user which has linked to his account a device that can track many metrics, but that lacks features of another model, such as a newer form factor, the ability to sync with a cellular device, and/or different aesthetic qualities such as color. This data is used in choosing an advertisement for this particular user. Other features that a user's device or devices may or may not have, but which could be used to inform the choice of an advertisement include, but are not limited to, GPS tracking, heart rate measurements, sleep state tracking and logging, blood pressure tracking and logging, and specific activity statistic tracking and logging such as swimming or biking.

Data about the user himself may also be used alone or in combination with device data to select advertisements. For example, if a user's gender is female, devices advertised to her are better adapted to couple to a female body and/or have aesthetics more commonly desirable for her gender. Metadata of data streams may also be used to inform the selection of an advertisement for a user. For example, if a user has made one or more manual data entries using their account website for a particular data type which is not tracked by their device, this user may be advertised a device which tracks that data type. In another example, a user who uses their device to track many different metrics and interacts with the website frequently is determined to be a data oriented user. Devices are advertised to this user that better cater to data oriented users, such as devices that have many features and require or invite significant interaction from the user to take advantage of all of the device features. Conversely, a user that rarely interacts with their device or website may be advertised a device that requires very little user interaction to acquire data.

In another embodiment, the data synthesizer is able to send electronic commands to other electronic devices based on data from one or multiple streams. In one example, the data synthesizer receives data from a location aware activity monitor in addition to a home thermostat. If the data synthesizer determines that the user is coming home from an activity, and that the temperature at home is not at a temperature which is comfortable, the data synthesizer sends a command to adjust the thermostat to achieve a comfortable temperature before the user gets home.

In another embodiment, the data synthesizer sends a command to the thermostat to lower the temperature before a user arrives home from a run, so that the home is comfortably cool when the user arrives. In another example, the thermostat may be adjusted to a lower temperature when it is detected that the user has left their home so as to save energy. This may be applied to multiple users of a household or apartment. For example, the thermostat may only be lowered when all of the users of the household are not home.

In another embodiment, the data synthesizer detects whether or not the user is in a vehicle and/or driving a vehicle. There may be an occupation detector in the car which communicates with the data synthesizer. For example, a vehicle detects that the user is in the vehicle if the user's weight is detected by a sensor in a seat in the car. The user is determined to be in a car by other means including but not limited to an accelerometer signal (in a device worn by the user) which is determined to be characteristic of being in a vehicle, a location signal which is characteristic of being in a vehicle (the user may be going at car speeds in a location associated with a road, for example), and a combination of multiple data streams characteristic of driving such as having a certain heart rate, stress level, and auditory signal.

The data synthesizer can take action on one or more streams of data measured while the user is in a vehicle. For example, if the data synthesizer determines that the user is drowsy or otherwise in an unsafe-to drive condition based on one or more data streams including but not limited to heart rate and accelerometer signals, the data synthesizer may alert the driver. The driver can be alerted by the device in one or more ways including but not limited to vibrating, making a sound, sending an auditory command, lighting up and/or displaying a message. In another example, the data synthesizer sends a command to the thermostat of the vehicle to adjust the temperature before or while the user is in the car.

FIG. 18 is a diagram of a website page for a device (e.g., a weight scale) which cannot track the number of floors climbed, according to one embodiment. Data about the device or devices connected to a user's account can also be used to help create recommendations or determine relevant advertisements about other devices. For example, in FIG. 18 the account owner does not have a device which can measure body weight and body fat linked to their account. This information is used to help determine the type of advertisement which may be most relevant to the user, in this case, an advertisement for a weight scale.

Figure 19:
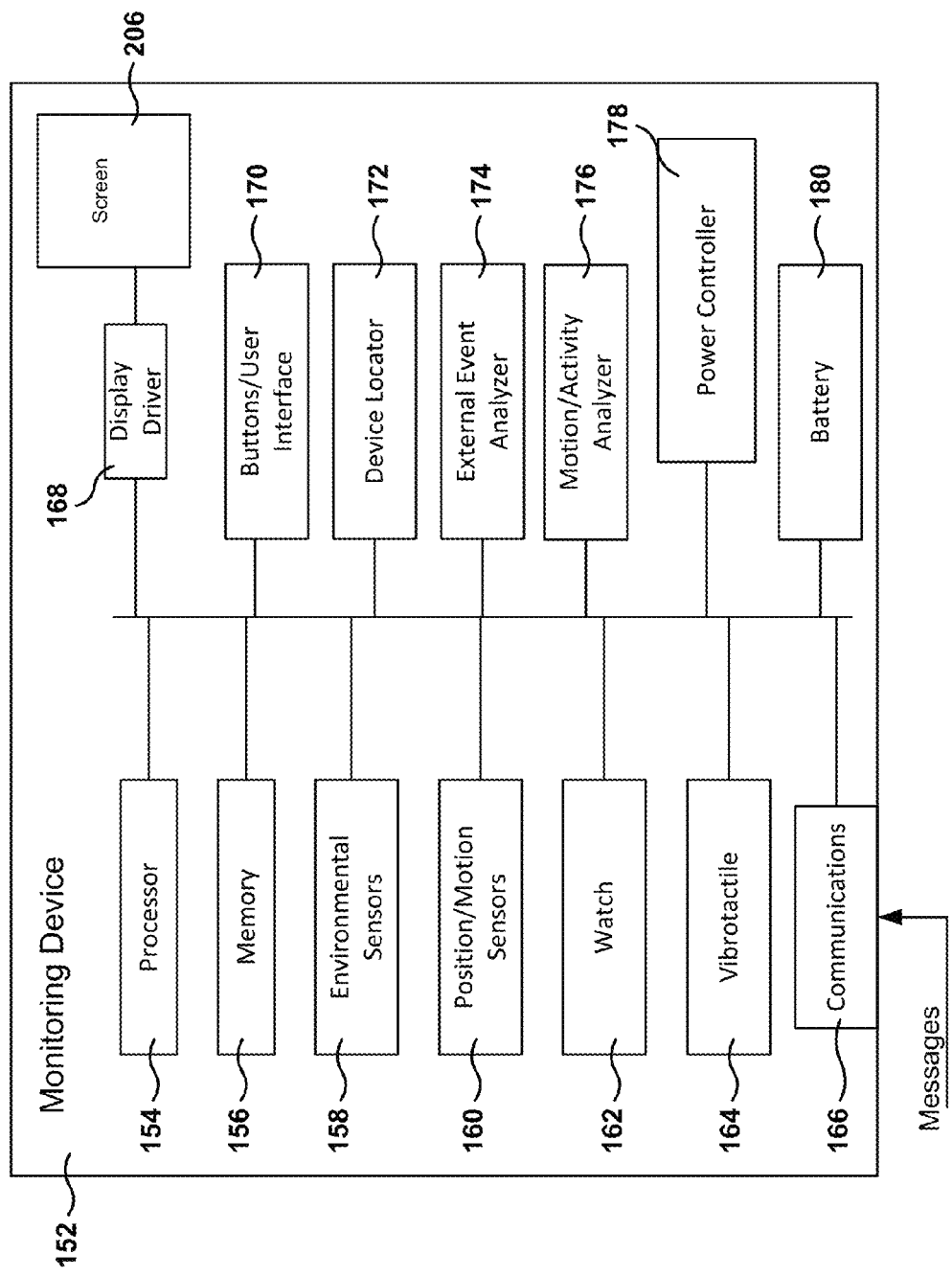
FIG. 19 is a simplified schematic diagram of a device for implementing embodiments described herein.

FIG. 19 is a simplified schematic diagram of a device for implementing embodiments described herein. The monitoring device 152 is an example of any of the monitoring devices described herein, and including a step tracker, a fitness tracker without buttons, or a fitness tracker defined to be clipped onto the belt of a user, etc. The monitoring device 152 includes processor 154, memory 156, one or more environmental sensors 158, one or more position and motion sensors 160, watch 162, vibrotactile feedback module 164, display driver 168, touchscreen 206, user interface/buttons 170, device locator 172, external event analyzer 174, motion/activity analyzer 176, power controller 178, and battery 180, all of which may be coupled to all or some of the other elements within monitoring device 152.

Examples of environmental sensors 158 include a barometric pressure sensor, a weather condition sensor, a light exposure sensor, a noise exposure sensor, a radiation exposure sensor, and a magnetic field sensor. Examples of a weather condition sensor include sensors for measuring temperature, humidity, pollen count, air quality, rain conditions, snow conditions, wind speed, or any combination thereof, etc. Examples of light exposure sensors include sensors for ambient light exposure, ultraviolet (UV) light exposure, or a combination thereof, etc. Examples of air quality sensors include sensors for measuring particulate counts for particles of different sizes, level of carbon dioxide in the air, level of carbon monoxide in the air, level of methane in the air, level of other volatile organic compounds in the air, or any combination thereof.

Examples of the position/motion sensor 160 include an accelerometer, a gyroscope, a rotary encoder, a calorie measurement sensor, a heat measurement sensor, a moisture measurement sensor, a displacement sensor, an ultrasonic sensor, a pedometer, an altimeter, a linear position sensor, an angular position sensor, a multi-axis position sensor, or any combination thereof, etc. In some embodiments, the position/motion sensor 160 measures a displacement (e.g., angular displacement, linear displacement, or a combination thereof, etc.) of the monitoring device 152 over a period of time with reference to a three-dimensional coordinate system to determine an amount of activity performed by the user during a period of time. In some embodiments, a position sensor includes a biological sensor, which is further described below.

The vibrotactile module 164 provides sensory output to the user by vibrating portable device 152. Further, the communications module 166 is operable to establish wired or wireless connections with other electronic devices to exchange data (e.g., activity data, geo-location data, location data, a combination thereof, etc.). Examples of wireless communication devices include, but are not limited to, a Wi-Fi adapter, a Bluetooth device, an Ethernet adapter, and infrared adapter, an ultrasonic adapter, etc.

The touchscreen 206 may be any type of display with touch sensitive functions. In another embodiment, a display is included but the display does not have touch-sensing capabilities. The touchscreen may be able to detect a single touch, multiple simultaneous touches, gestures defined on the display, etc. The display driver 168 interfaces with the touchscreen 206 for performing input/output operations. In one embodiment, display driver 168 includes a buffer memory for storing the image displayed on touchscreen 206.

The buttons/user interface may include buttons, switches, cameras, USB ports, keyboards, or any other device that can provide input or output functions.

Device locator 172 provides capabilities for acquiring data related to the location (absolute or relative) of monitoring device 152. Examples device locators 172 include a GPS transceiver, a mobile transceiver, a dead-reckoning module, a camera, etc. As used herein, a device locator may be referred to as a device or circuit or logic that can generate geo-location data. The geo-location data provides the absolute coordinates for the location of the monitoring device 152. The coordinates may be used to place the monitoring device 152 on a map, in a room, in a building, etc. in some embodiments, a GPS device provides the geo-location data. In other embodiments, the geo-location data can be obtained or calculated from data acquired from other devices (e.g., cell towers, Wi-Fi device signals, other radio signals, etc.), which can provide data points usable to locate or triangulate a location.

External event analyzer 174 receives data regarding the environment of the user and determines external events that might affect the power consumption of the user. For example, the external event analyzer 174 may determine low light conditions in a room, and assume that there is a high probability that the user is sleeping. In addition, the external event analyzer 174 may also receive external data, such as GPS location from a smart phone, and determine that the user is on a vehicle and in motion.

In some embodiments, the processor 154 receives one or more geo-locations measured by the device locator 172 over a period of time and determines a location of the monitoring device 152 based on the geo-locations and/or based on one or more selections made by the user, or based on information available within a geo-location-location database of the network. For example, the processor 154 may compare the current location of the monitoring device against known locations in a location database, to identify presence in well-known points of interest to the user or to the community. In one embodiment, upon receiving the geo-locations from the device locator 172, the processor 154 determines the location based on the correspondence between the geo-locations and the location in the geo-location-location database.

The one or more environmental sensors 158 may sense and determine one or more environmental parameters (e.g., barometric pressure, weather condition, amount of light exposure, noise levels, radiation levels, magnetic field levels, or a combination thereof, etc.) of an environment in which the monitoring device is placed.

The watch 162 is operable to determine the amount of time elapsed between two or more events. In one embodiment, the events are associated with one or more positions sensed by the position sensor 160, associated with one or more environmental parameters determined by the environmental sensor 158, associated with one or more geo-locations determined by the device locator 172, and/or associated with one or more locations determined by the processor 154.

Power controller 178 manages and adjusts one or more power operational parameters defined for the monitoring device 152. In one embodiment, the power operational parameters include options for managing the touchscreen 206, such as by determining when to turn ON or OFF the touchscreen, scan rate, brightness, etc. In addition, the power controller 178 is operable to determine other power operational parameters, besides the parameters associated with the touchscreen, such as determining when to turn ON or OFF other modules (e.g., GPS, environmental sensors, etc.) or limiting the frequency of use for one or more of the modules within monitoring device 152.

Monitoring device 152 may have a variety of internal states and/or events which may dynamically change the characteristics of the touchscreen or of other modules. These states may include one or more of the following:

Battery level
Notifications/Prompting of user interaction
Alarm
Timer elapsed
Email received/sent
Instant Message received/sent
Text message received/sent
Calendar event
Physiological goal met (e.g., 10,000 steps reached in the day)
Non-physiological goal met (e.g., completed a to-do item)
Application notifications
Music player notifications (e.g., song ended/started, playlist ended/started)
User Interface
Layout of virtual buttons on the touchscreen
Expected user interaction based on what is displayed and/or the application in the foreground of the operating system.
   Expected user touch speed (e.g., fast for typing or playing a game, slow for reading an article)
   Expected user touch area
   Expected user touch trajectory (e.g., some games require long, straight swipes, while applications that take text input may require a touch to one specific area with little or no trajectory).
User interaction through non-touchscreen inputs
User pressing a button
User touching a capacitive touch sensor not integrated into the touchscreen
User activating a proximity sensor
Sensors which detect the user attempting to interact with the screen
   Force transducer under the screen
   Gyroscope, magnetometer, and/or accelerometer located near the screen
   Pressure transducer to measure change in pressure due to housing deflection when user presses on or near the screen
   Tap or initial touch detection using one or more or a combination of: accelerometers, piezoelectric sensors, motion sensors, pressure sensors, force sensors
User Characteristics
Gender
Age
Weight
Geographical location (e.g., urban area, rural area, country, city, town, exact address and or GPS coordinates)
   Current location
   Residence location
   Work location It is noted that these states may be communicated to the user through one or more methods including, but not limited to, displaying them visually, outputting an audio alert, and/or haptic feedback.

In some embodiments, data analysis of data produced by different modules may be performed in monitoring device 152, in other device in communication with monitoring device 152, or in combination of both devices. For example, the monitoring device may be generating a large amount of data related to the heart rate of the user. Before transmitting the data, the monitoring device 152 may process the large amount of data to synthesize information regarding the heart rate, and then the monitoring device 152 may send the data to a server that provides an interface to the user. For example, the monitoring device may provide summaries of the heart rate in periods of one minute, 30 seconds, five minutes, 50 minutes, or any other time period. By performing some calculations in the monitoring device 152, the processing time required to be performed on the server is decreased.

Some other data may be sent in its entirety to another device, such as steps the user is taken, or periodical updates on the location of the monitoring device 152. Other calculations may be performed in the server, such as analyzing data from different modules to determine stress levels, possible sickness by the user, etc.

It is noted that the embodiments illustrated in FIG. 19 are exemplary. Other embodiments may utilize different modules, additional modules, or a subset of modules. In addition, some of the functionality of two different modules might be combined in a single module, or the functionality of a single module might be spread over a plurality of components. The embodiments illustrated in FIG. 19 should therefore not be interpreted to be exclusive or limiting, but rather exemplary or illustrative.

Figure 20:
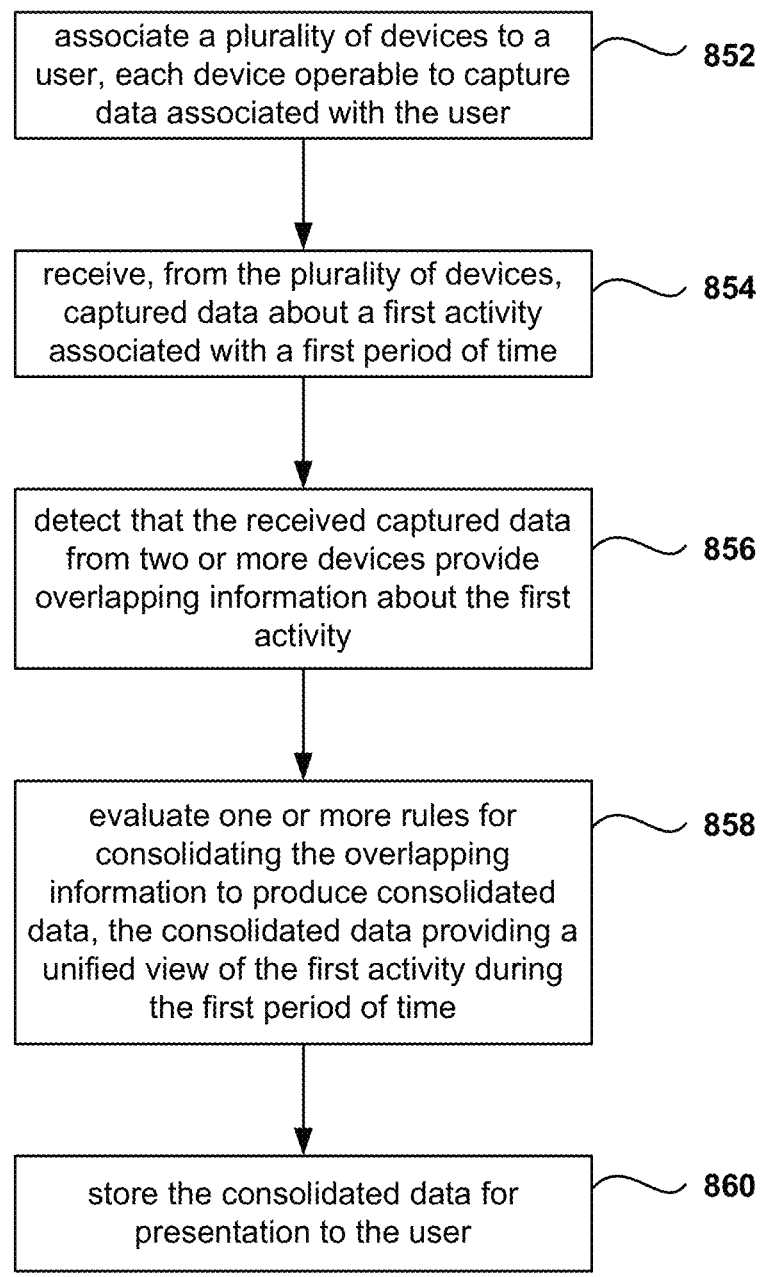
FIG. 20 is a flowchart illustrating an algorithm for performing data synthesis for data provided by a plurality of devices, according to one embodiment.

FIG. 20 is a flowchart illustrating an algorithm for performing data synthesis for data provided by a plurality of devices, according to one embodiment. In operation 852, a plurality of devices is associated with a user, each device being operable to capture data associated with the user.

From operation 852 the method flows to operation 854, where captured data is received from the plurality of devices, the captured data being about a first activity associated with a first period of time. From operation 854 the method flows to operation 856, where a detection takes place regarding the received captured data from two or more devices provides overlapping information about the first activity.

From operation 856 the method flows to operation 858, where one or more rules are evaluated, the one or more rules being for consolidating the overlapping information to produce consolidated data. The consolidated data provides a unified view of the first activity during the first period of time.

From operation 858 the method flows to operation 860 for storing the consolidated data for presentation to the user. In one embodiment, the operations of the method are executed by a processor.

Figure 21:
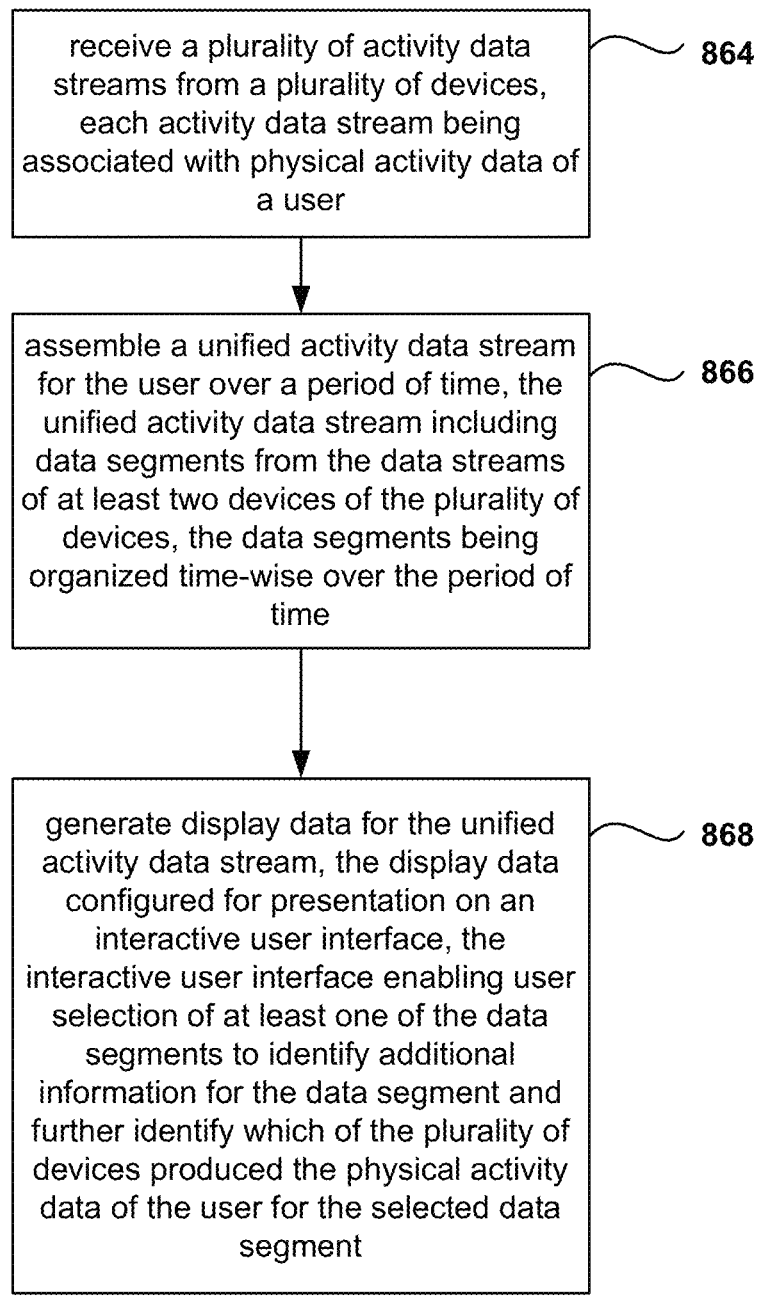
FIG. 21 is a flowchart illustrating an algorithm for creating a unified data stream from a plurality of data streams acquired from a plurality of devices, according to one embodiment.

FIG. 21 is a flowchart illustrating an algorithm for creating a unified data stream from a plurality of data streams acquired from a plurality of devices, according to one embodiment. In operation 864, a plurality of activity data streams are received from a plurality of devices, each activity data stream being associated with physical activity data of a user.

From operation 864 the method flows to operation 866, which is an operation for assembling a unified activity data stream for the user over a period of time. That unified activity data stream includes data segments from the data streams of at least two devices of the plurality of devices, and the data segments are organized time-wise over the period of time. As used herein, a time-wise organization of data segments refers to the aggregation of data from multiple devices based on the time associated with the data. In one embodiment, the data includes physical activity data of the user tagged with the timestamp for the time when the activity took place. As a result, the unified activity data stream includes data segments with respective time tags identifying the time associated with the data segment.

From operation 866 the method flows to operation 868, which is an operation for generating display data for the unified activity data stream. The display data is configured for presentation on an interactive user interface, and the interactive user interface enables user selection of at least one of the data segments to identify additional information for the data segment, and to further identify which of the plurality of devices produced the physical activity data of the user for the selected data segment. In one embodiment, the operations of the method are executed by a processor.

While the various operations in this flowchart are presented and described sequentially, one of ordinary skill will appreciate that some or all of the operations may be executed in a different order, be combined or omitted, or be executed in parallel.

Figure 22:
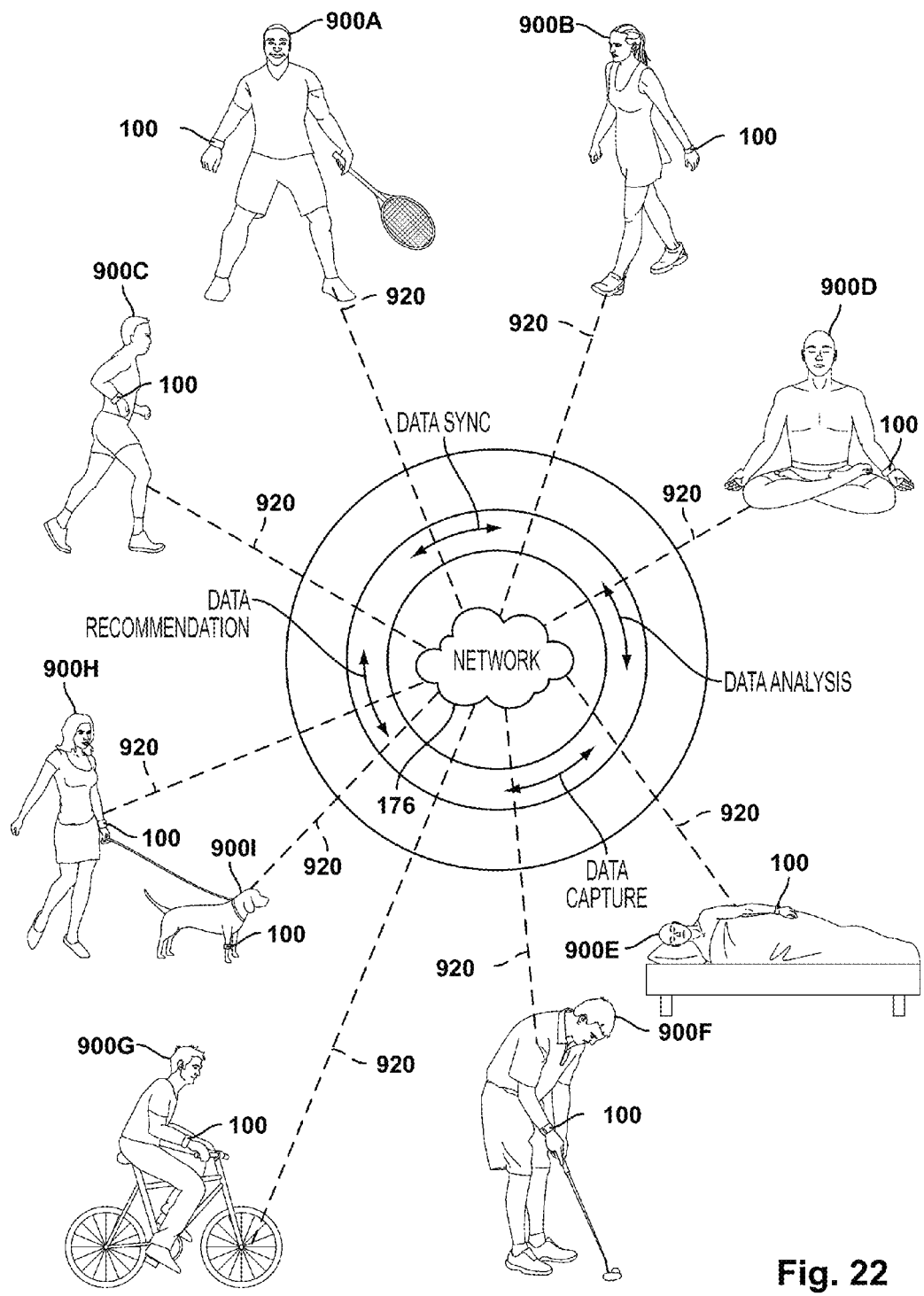
FIG. 22 illustrates an example where various types of activities of users can be captured or collected by activity tracking devices, in accordance with various embodiments of the present invention.

FIG. 22 illustrates an example where various types of activities of users 900A-900I can be captured or collected by activity tracking devices, in accordance with various embodiments of the present embodiments. As shown, the various types of activities can generate different types of data that can be captured by the activity tracking device 100. The data, which can be represented as motion data (or processed motion data) can be transferred 920 to a network 176 for processing and saving by a server, as described above. In one embodiment, the activity tracking device 100 can communicate to a device using a wireless connection, and the device is capable of communicating and synchronizing the captured data with an application running on the server. In one embodiment, an application running on a local device, such as a smart phone or tablet or smart watch can capture or receive data from the activity tracking device 100 and represent the tract motion data in a number of metrics.

In one embodiment, the device collects one or more types of physiological and/or environmental data from embedded sensors and/or external devices and communicates or relays such metric information to other devices, including devices capable of serving as Internet-accessible data sources, thus permitting the collected data to be viewed, for example, using a web browser or network-based application. For example, while the user is wearing an activity tracking device, the device may calculate and store the user's step count using one or more sensors. The device then transmits data representative of the user's step count to an account on a web service, computer, mobile phone, or health station where the data may be stored, processed, and visualized by the user. Indeed, the device may measure or calculate a plurality of other physiological metrics in addition to, or in place of, the user's step count.

Some physiological metrics include, but are not limited to, energy expenditure (for example, calorie burn), floors climbed and/or descended, heart rate, heart rate variability, heart rate recovery, location and/or heading (for example, through GPS), elevation, ambulatory speed and/or distance traveled, swimming lap count, bicycle distance and/or speed, blood pressure, blood glucose, skin conduction, skin and/or body temperature, electromyography, electroencephalography, weight, body fat, caloric intake, nutritional intake from food, medication intake, sleep periods (i.e., clock time), sleep phases, sleep quality and/or duration, pH levels, hydration levels, and respiration rate. The device may also measure or calculate metrics related to the environment around the user such as barometric pressure, weather conditions (for example, temperature, humidity, pollen count, air quality, rain/snow conditions, wind speed), light exposure (for example, ambient light, UV light exposure, time and/or duration spent in darkness), noise exposure, radiation exposure, and magnetic field.

Still further, other metrics can include, without limitation, calories burned by a user, weight gained by a user, weight lost by a user, stairs ascended, e.g., climbed, etc., by a user, stairs descended by a user, steps taken by a user during walking or running, a number of rotations of a bicycle pedal rotated by a user, sedentary activity data, driving a vehicle, a number of golf swings taken by a user, a number of forehands of a sport played by a user, a number of backhands of a sport played by a user, or a combination thereof. In some embodiments, sedentary activity data is referred to herein as inactive activity data or as passive activity data. In some embodiments, when a user is not sedentary and is not sleeping, the user is active. In some embodiments, a user may stand on a monitoring device that determines a physiological parameter of the user. For example, a user stands on a scale that measures a weight, a body fat percentage, a biomass index, or a combination thereof, of the user.

Furthermore, the device or the system collating the data streams may calculate metrics derived from this data. For example, the device or system may calculate the user's stress and/or relaxation levels through a combination of heart rate variability, skin conduction, noise pollution, and sleep quality. In another example, the device or system may determine the efficacy of a medical intervention (for example, medication) through the combination of medication intake, sleep and/or activity data. In yet another example, the device or system may determine the efficacy of an allergy medication through the combination of pollen data, medication intake, sleep and/or activity data. These examples are provided for illustration only and are not intended to be limiting or exhaustive.

This information can be associated to the users account, which can be managed by an activity management application on the server. The activity management application can provide access to the users account and data saved thereon. The activity manager application running on the server can be in the form of a web application. The web application can provide access to a number of websites screens and pages that illustrate information regarding the metrics in various formats. This information can be viewed by the user, and synchronized with a computing device of the user, such as a smart phone.

In one embodiment, the data captured by the activity tracking device 100 is received by the computing device, and the data is synchronized with the activity measured application on the server. In this example, data viewable on the computing device (e.g., smart phone) using an activity tracking application (app) can be synchronized with the data present on the server, and associated with the user's account. In this way, information entered into the activity tracking application on the computing device can be synchronized with application illustrated in the various screens of the activity management application provided by the server on the website.

The user can therefore access the data associated with the user account using any device having access to the Internet. Data received by the network 176 can then be synchronized with the user's various devices, and analytics on the server can provide data analysis to provide recommendations for additional activity, and or improvements in physical health. The process therefore continues where data is captured, analyzed, synchronized, and recommendations are produced. In some embodiments, the captured data can be itemized and partitioned based on the type of activity being performed, and such information can be provided to the user on the website via graphical user interfaces, or by way of the application executed on the users smart phone (by way of graphical user interfaces).

In one embodiment, the sensor or sensors of a device 100 can determine or capture data to determine an amount of movement of the monitoring device over a period of time. The sensors can include, for example, an accelerometer, a magnetometer, a gyroscope, or combinations thereof. Broadly speaking, these sensors are inertial sensors, which capture some movement data, in response to the device 100 being moved. The amount of movement (e.g., motion sensed) may occur when the user is performing an activity of climbing stairs over the time period, walking, running, etc. The monitoring device may be worn on a wrist, carried by a user, worn on clothing (using a clip, or placed in a pocket), attached to a leg or foot, attached to the user's chest, waist, or integrated in an article of clothing such as a shirt, hat, pants, blouse, glasses, and the like. These examples are not limiting to all the possible ways the sensors of the device can be associated with a user or thing being monitored.

In other embodiments, a biological sensor can determine any number of physiological characteristics of a user. As another example, the biological sensor may determine heart rate, a hydration level, body fat, bone density, fingerprint data, sweat rate, and/or a bioimpedance of the user. Examples of the biological sensors include, without limitation, a biometric sensor, a physiological parameter sensor, a pedometer, or a combination thereof.

In some embodiments, data associated with the user's activity can be monitored by the applications on the server and the users device, and activity associated with the user's friends, acquaintances, or social network peers can also be shared, based on the user's authorization. This provides for the ability for friends to compete regarding their fitness, achieve goals, receive badges for achieving goals, get reminders for achieving such goals, rewards or discounts for achieving certain goals, etc.

As noted, an activity tracking device 100 can communicate with a computing device (e.g., a smartphone, a tablet computer, a desktop computer, or computer device having wireless communication access and/or access to the Internet). The computing device, in turn, can communicate over a network, such as the Internet or an Intranet to provide data synchronization. The network may be a wide area network, a local area network, or a combination thereof. The network may be coupled to one or more servers, one or more virtual machines, or a combination thereof. A server, a virtual machine, a controller of a monitoring device, or a controller of a computing device is sometimes referred to herein as a computing resource. Examples of a controller include a processor and a memory device.

In one embodiment, the processor may be a general purpose processor. In another embodiment, the processor can be a customized processor configured to run specific algorithms or operations. Such processors can include digital signal processors (DSPs), which are designed to execute or interact with specific chips, signals, wires, and perform certain algorithms, processes, state diagrams, feedback, detection, execution, or the like. In some embodiments, a processor can include or be interfaced with an application specific integrated circuit (ASIC), a programmable logic device (PLD), a central processing unit (CPU), or a combination thereof, etc.

In some embodiments, one or more chips, modules, devices, or logic can be defined to execute instructions or logic, which collectively can be viewed or characterized to be a processor. Therefore, it should be understood that a processor does not necessarily have to be one single chip or module, but can be defined from a collection of electronic or connecting components, logic, firmware, code, and combinations thereof.

Examples of a memory device include a random access memory (RAM) and a read-only memory (ROM). A memory device may be a Flash memory, a redundant array of disks (RAID), a hard disk, or a combination thereof.

Embodiments described in the present disclosure may be practiced with various computer system configurations including hand-held devices, microprocessor systems, microprocessor-based or programmable consumer electronics, minicomputers, mainframe computers and the like. Several embodiments described in the present disclosure can also be practiced in distributed computing environments where tasks are performed by remote processing devices that are linked through a wire-based or wireless network.

With the above embodiments in mind, it should be understood that a number of embodiments described in the present disclosure can employ various computer-implemented operations involving data stored in computer systems. These operations are those requiring physical manipulation of physical quantities. Any of the operations described herein that form part of various embodiments described in the present disclosure are useful machine operations. Several embodiments described in the present disclosure also relate to a device or an apparatus for performing these operations. The apparatus can be specially constructed for a purpose, or the apparatus can be a computer selectively activated or configured by a computer program stored in the computer. In particular, various machines can be used with computer programs written in accordance with the teachings herein, or it may be more convenient to construct a more specialized apparatus to perform the required operations.

Various embodiments described in the present disclosure can also be embodied as computer-readable code on a non-transitory computer-readable medium. The computer-readable medium is any data storage device that can store data, which can thereafter be read by a computer system. Examples of the computer-readable medium include hard drives, network attached storage (NAS), ROM, RAM, compact disc-ROMs (CD-ROMs), CD-recordables (CD-Rs), CD-rewritables (RWs), magnetic tapes and other optical and non-optical data storage devices. The computer-readable medium can include computer-readable tangible medium distributed over a network-coupled computer system so that the computer-readable code is stored and executed in a distributed fashion.

Although the method operations were described in a specific order, it should be understood that other housekeeping operations may be performed in between operations, or operations may be performed in an order other than that shown, or operations may be adjusted so that they occur at slightly different times, or may be distributed in a system which allows the occurrence of the processing operations at various intervals associated with the processing.

Although the foregoing embodiments have been described in some detail for purposes of clarity of understanding, it will be apparent that certain changes and modifications can be practiced within the scope of the appended claims. Accordingly, the present embodiments are to be considered as illustrative and not restrictive, and the various embodiments described in the present disclosure are not to be limited to the details given herein, but may be modified within the scope and equivalents of the appended claims.

What is claimed is:

1. A method comprising:
receiving a plurality of activity data streams from a plurality of devices, each activity data stream being associated with physical activity data of a user; and
assembling a unified activity data stream for the user over a period of time, the unified activity data stream including data segments from the data streams of at least two devices of the plurality of devices, the data segments being organized time-wise over the period of time, wherein assembling the unified activity data stream further includes:
detecting a first time period with data available from two or more devices;
identifying a priority for each of the two or more devices; and
adding to the unified activity data stream a first data segment covering the first time period, the first data segment having the data from a device with a higher priority from two or more devices, wherein operations of the method are executed by a processor.

2. A method comprising:
receiving a plurality of activity data streams from a plurality of devices, each activity data stream being associated with physical activity data of a user; and
assembling a unified activity data stream for the user over a period of time, the unified activity data stream including data segments from the data streams of at least two devices of the plurality of devices, the data segments being organized time-wise over the period of time, wherein assembling the unified activity data stream further includes:
detecting a second time period with data available from a single device from the plurality of devices; and
adding to the unified activity data stream a second data segment covering the second time period, the second data segment having the data from the single device, wherein operations of the method are executed by a processor.

3. A method comprising:
receiving a plurality of activity data streams from a plurality of devices, each activity data stream being associated with physical activity data of a user; and
assembling a unified activity data stream for the user over a period of time, the unified activity data stream including data segments from the data streams of at least two devices of the plurality of devices, the data segments being organized time-wise over the period of time
generating display data for the unified activity data stream, the display data configured for presentation on an interactive user interface, the interactive user interface enabling user selection of at least one of the data segments to identify additional information for the data segment and further identify which of the plurality of devices produced the physical activity data of the user for the selected data segment, wherein operations of the method are executed by a processor.

4. The method as recited in claim 3, further including:
identifying an activity being performed by the user during at least one of the data segments; and
presenting the activity in the interactive user interface.

5. The method as recited in claim 4, wherein identifying the activity being performed by the user is calculated based on one or more of data in a calendar of the user, or a pattern found in the data of one or more devices from the plurality of devices, or information entered by the user regarding the activity.

6. A method comprising:
receiving a plurality of activity data streams from a plurality of devices, each activity data stream being associated with physical activity data of a user; and
assembling a unified activity data stream for the user over a period of time, the unified activity data stream including data segments from the data streams of at least two devices of the plurality of devices, the data segments being organized time-wise over the period of time
sending at least part of the unified activity data stream to one or more of the plurality of devices, wherein operations of the method are executed by a processor.

7. A method comprising:
receiving a plurality of activity data streams from a plurality of devices, each activity data stream being associated with physical activity data of a user; and
assembling a unified activity data stream for the user over a period of time, the unified activity data stream including data segments from the data streams of at least two devices of the plurality of devices, the data segments being organized time-wise over the period of time
analyzing the unified activity data stream to identify a stride length of the user; and
sending the stride length of the user to one or more devices from the plurality of devices, wherein operations of the method are executed by a processor.

8. A method comprising:
receiving a plurality of activity data streams from a plurality of devices, each activity data stream being associated with physical activity data of a user; and
assembling a unified activity data stream for the user over a period of time, the unified activity data stream including data segments from the data streams of at least two devices of the plurality of devices, the data segments being organized time-wise over the period of time
parsing the received plurality of data streams, before assembling the unified activity data stream, to identify data types and respective data values in the data streams, wherein operations of the method are executed by a processor.

9. A method comprising:
receiving data streams regarding activity of a user, each data stream being associated with a respective device of a plurality of devices;
evaluating one or more rules for consolidating the data streams into a unified activity data stream, wherein evaluating the one or more rules further includes:
identifying first time segments where data is available from a single device from the plurality of devices;
adding the available data to the unified activity data stream for the first time segments;
identifying second time segments where data exists from two or more devices from the plurality of devices; and
adding data to the second time segments based on the existing data from the two or more devices and based on the one or more rules; and
storing the unified activity data stream for presentation to the user, wherein operations of the method are executed by a processor.

10. The method as recited in claim 9, wherein adding data to the second time segments further includes:
identifying a priority for each of the plurality of devices; and
for each second time segment, selecting the data from a device with a highest priority from the plurality of devices having data for the second time segment.

11. The method as recited in claim 9, wherein adding data to the second time segments further includes:
for each second time segment, calculating a statistical measure of the data from devices having data for the second time segment, wherein the statistical measure is one of mean, or mode, or median, or maximum, or minimum; and
adding the calculated statistical measure to the unified activity data stream for the respective second time segment.

12. The method as recited in claim 9, wherein adding data to the second time segments further includes:
for each second time segment, calculating unified data for the respective second time segment according to a voting system that selects data based on a grouping of the data, wherein the voting system identifies clusters of data points and selects a cluster with most data points.

13. The method as recited in claim 9, wherein the evaluating the one or more rules further includes:
identifying an activity being performed by the user, wherein at least one of the rules from the one or more rules is based on which activity is being performed by the user.

14. The method as recited in claim 9, wherein each rule includes a trigger and an action, wherein the trigger includes one or more conditions, wherein the action is performed based on the one or more conditions.

15. The method as recited in claim 9, further including:
sending at least part of the unified activity data stream the one or more of the plurality of devices.

16. The method as recited in claim 9, further including:
analyzing the unified activity data stream to identify a stride length of the user; and
sending the stride length of the user to one or more devices from the plurality of devices.

17. The method as recited in claim 9, further including:
receiving environmental data about an environment of the user, wherein at least one rule from the one or more rules is based on the environmental data.

18. The method as recited in claim 9, wherein operations of the method are performed by a computer program when executed by one or more processors, the computer program being embedded in a non-transitory computer-readable storage medium.

19. The method as recited in claim 9, further including:
detecting that the user is performing a joint activity with a friend; and
adding exercise data received from a device associated with the friend to the unified activity data stream.

20. A server comprising:
a communications module operable to receive a plurality of activity data streams from a plurality of devices, each activity data stream being associated with physical activity data of a user;
a memory for storing the plurality of activity data streams and a unified activity data stream that includes data segments from the data streams of at least two devices of the plurality of devices; and
a processor operable to assemble the unified activity data stream for the user over a period of time, the data segments being organized time-wise over the period of time, wherein the processor generates display data for the unified activity data stream, the display data configured for presentation on an interactive user interface, the interactive user interface enabling user selection of at least one of the data segments to identify additional information for the data segment and further identify which of the plurality of devices produced the physical activity data of the user for the selected data segment, wherein the interactive user interface includes one or more of an activity summary, the activity summary including a number of steps taken daily, a number of floors climbed daily, a distance traveled daily, or a number of calories burned daily.

21. The server as recited in claim 20, wherein the interactive user interface provides options to the user for selecting which devices to include in the unified activity data stream, and for prioritizing the devices for inclusion in the unified activity data stream.

22. The server as recited in claim 20, wherein the interactive user interface includes an activity display interface including:
activities detected during a day; and
a graphical representation identifying activity levels throughout the day.

23. A server comprising:
a communications module operable to receive a plurality of activity data streams from a plurality of devices, each activity data stream being associated with physical activity data of a user;
a memory for storing the plurality of activity data streams and a unified activity data stream that includes data segments from the data streams of at least two devices of the plurality of devices; and
a processor operable to assemble the unified activity data stream for the user over a period of time, the data segments being organized time-wise over the period of time, wherein the server is coupled to a time series database for storing the plurality of activity data streams and the unified activity data stream.

24. A server comprising:
a communications module operable to receive a plurality of activity data streams from a plurality of devices, each activity data stream being associated with physical activity data of a user;
a memory for storing the plurality of activity data streams and a unified activity data stream that includes data segments from the data streams of at least two devices of the plurality of devices; and
a processor operable to assemble the unified activity data stream for the user over a period of time, the data segments being organized time-wise over the period of time, wherein the processor assembles the unified activity data stream by utilizing one or more rules, each rule including a trigger and an action, wherein the trigger includes one or more conditions, wherein the action is performed based on the one or more conditions.

25. A server comprising:
a communications module operable to receive a plurality of activity data streams from a plurality of devices, each activity data stream being associated with physical activity data of a user;
a memory for storing the plurality of activity data streams and a unified activity data stream that includes data segments from the data streams of at least two devices of the plurality of devices; and
a processor operable to assemble the unified activity data stream for the user over a period of time, the data segments being organized time-wise over the period of time, wherein the unified activity data stream is associated with a measurement selected from a group consisting of steps taken, energy expenditure, vertical distance ascended or descended, heart rate, heart rate variability, heart rate recovery, location, heading, elevation, speed, distance traveled, swimming laps, blood pressure, blood glucose, skin conduction, body temperature, electromyography, electroencephalography, weight, body fat, caloric intake, medication intake, sleep state, sleep phase, sleep quality, sleep duration, or restoration rate.

26. A non-transitory computer-readable storage medium storing a computer program, the computer-readable storage medium comprising:
program instructions for receiving a plurality of activity data streams from a plurality of devices, each activity data stream being associated with physical activity data of a user; and
program instructions for assembling a unified activity data stream for the user over a period of time, the unified activity data stream including data segments from the data streams of at least two devices of the plurality of devices, the data segments being organized time-wise over the period of time, wherein assembling the unified activity data stream further includes:
program instructions for detecting a first time period with data available from two or more devices;
program instructions for identifying a priority for each of the two or more devices;
program instructions for adding to the unified activity data stream a first data segment covering the first time period, the first data segment having the data from a device with a highest priority from two or more devices;
program instructions for detecting a second time period with data available from a single device from the plurality of devices; and
program instructions for adding to the unified activity data stream a second data segment covering the second time period, the second data segment having the data from the single device.

27. A non-transitory computer-readable storage medium storing a computer program, the computer-readable storage medium comprising:
program instructions for receiving a plurality of activity data streams from a plurality of devices, each activity data stream being associated with physical activity data of a user; and
program instructions for assembling a unified activity data stream for the user over a period of time, the unified activity data stream including data segments from the data streams of at least two devices of the plurality of devices, the data segments being organized time-wise over the period of time; and
program instructions for generating display data for the unified activity data stream, the display data configured for presentation on an interactive user interface, the interactive user interface enabling user selection of at least one of the data segments to identify additional information for the data segment and further identify which of the plurality of devices produced the physical activity data of the user for the selected data segment.

* * * * *